United States Patent
Euteneuer et al.

(10) Patent No.: US 10,449,031 B2
(45) Date of Patent: Oct. 22, 2019

(54) METHODS AND APPARATUS FOR DELIVERING AND POSITIONING SHEET-LIKE MATERIALS

(71) Applicant: Rotation Medical, Inc., Plymouth, MN (US)

(72) Inventors: Charles L. Euteneuer, St. Michael, MN (US); John Quackenbush, North Oaks, MN (US)

(73) Assignee: Rotation Medical, Inc., Plymouth, MN (US)

( * ) Notice: Subject to any disclaimer, the term of this patent is extended or adjusted under 35 U.S.C. 154(b) by 499 days.

(21) Appl. No.: 14/657,163

(22) Filed: Mar. 13, 2015

(65) Prior Publication Data

US 2015/0182326 A1    Jul. 2, 2015

Related U.S. Application Data

(63) Continuation of application No. 14/506,029, filed on Oct. 3, 2014, now Pat. No. 9,005,224, which is a
(Continued)

(51) Int. Cl.
*A61F 2/02* (2006.01)
*A61F 2/08* (2006.01)
(Continued)

(52) U.S. Cl.
CPC .......... *A61F 2/0805* (2013.01); *A61F 2/0063* (2013.01); *A61F 2/0811* (2013.01);
(Continued)

(58) Field of Classification Search
CPC .... A61F 2/0805; A61F 2/0811; A61F 2/0063; A61F 2002/0072
See application file for complete search history.

(56) References Cited

U.S. PATENT DOCUMENTS

| 511,238 A | 12/1893 | Hietzman |
| 765,793 A | 7/1904 | Ruckel |
(Continued)

FOREIGN PATENT DOCUMENTS

| CA | 2390508 A1 | 5/2001 |
| EP | 0142225 A1 | 5/1985 |
(Continued)

OTHER PUBLICATIONS

Euteneuer et al.; U.S. Appl. No. 13/889,675 entitled "Metods and Apparatus for Fixing Sheet-Like Materials to a Target Tissue," filed May 8, 2013.
(Continued)

*Primary Examiner* — Anh T Dang
(74) *Attorney, Agent, or Firm* — Seager, Tufte & Wickhem LLP

(57) ABSTRACT

An implant delivery system for delivering a sheet-like implant is disclosed. The device includes an implant spreader assembly disposed proximate the distal end of a delivery shaft. The implant spreader assembly includes a first arm and a second arm. The arms are coupled to the delivery shaft such that the first arm and second arm are moveable between a closed position and an open position. When the first and second arms are in the closed position, the arms extend generally in the longitudinal direction. When pivoting to the open position the distal end of each arm travels in a generally transverse direction to spread a sheet-like implant.

15 Claims, 22 Drawing Sheets

Related U.S. Application Data continuation of application No. 13/397,603, filed on Feb. 15, 2012, now Pat. No. 8,864,780.

(60) Provisional application No. 61/443,169, filed on Feb. 15, 2011.

(51) Int. Cl.
  *A61F 2/00* (2006.01)
  *A61B 17/00* (2006.01)
  *A61B 17/29* (2006.01)

(52) U.S. Cl.
  CPC . *A61B 17/00234* (2013.01); *A61B 2017/2944* (2013.01); *A61F 2/08* (2013.01); *A61F 2002/0072* (2013.01); *A61F 2002/0817* (2013.01); *A61F 2220/0025* (2013.01); *A61F 2220/0033* (2013.01)

(56) References Cited

U.S. PATENT DOCUMENTS

| | | |
|---|---|---|
| 1,728,316 A | 9/1929 | Von Wachenfeldt |
| 1,855,546 A | 4/1932 | File |
| 1,868,100 A | 7/1932 | Goodstein |
| 1,910,688 A | 5/1933 | Goodstein |
| 1,940,351 A | 12/1933 | Howard |
| 2,034,785 A | 3/1936 | Charles |
| 2,075,508 A | 3/1937 | Davidson |
| 2,131,321 A | 9/1938 | Wilber |
| 2,158,242 A | 5/1939 | Maynard |
| 2,199,025 A | 4/1940 | Conn |
| 2,201,610 A | 5/1940 | Dawson, Jr. |
| 2,254,620 A | 9/1941 | Miller |
| 2,277,931 A | 3/1942 | Moe |
| 2,283,814 A | 5/1942 | Place |
| 2,316,297 A | 4/1943 | Southerland et al. |
| 2,421,193 A | 5/1947 | James |
| 2,571,813 A | 10/1951 | Austin |
| 2,630,316 A | 3/1953 | Foster |
| 2,684,070 A | 7/1954 | Kelsey |
| 2,744,251 A | 5/1956 | Leonhard |
| 2,790,341 A | 4/1957 | Keep et al. |
| 2,817,339 A | 12/1957 | Sullivan |
| 2,825,162 A | 3/1958 | Flood |
| 2,881,762 A | 4/1959 | Lowrie |
| 2,910,067 A | 10/1959 | White |
| 3,068,870 A | 12/1962 | Abraham |
| 3,077,812 A | 2/1963 | Gerhard |
| 3,103,666 A | 9/1963 | Bone |
| 3,123,077 A | 3/1964 | Alcamo |
| 3,209,754 A | 10/1965 | Brown |
| 3,221,746 A | 12/1965 | William |
| 3,470,834 A | 10/1969 | Bone |
| 3,527,223 A | 9/1970 | Shein |
| 3,570,497 A | 3/1971 | Lemole |
| 3,577,837 A | 5/1971 | Bader, Jr. |
| 3,579,831 A | 5/1971 | Stevens et al. |
| 3,643,851 A | 2/1972 | Green et al. |
| 3,687,138 A | 8/1972 | Jarvik |
| 3,716,058 A | 2/1973 | Tanner |
| 3,717,294 A | 2/1973 | Green |
| 3,757,629 A | 9/1973 | Scheider |
| 3,777,538 A | 12/1973 | Weatherly et al. |
| 3,837,555 A | 9/1974 | Green |
| 3,845,772 A | 11/1974 | Smith |
| 3,875,648 A | 4/1975 | Bone |
| 3,960,147 A | 6/1976 | Murray |
| 3,976,079 A | 8/1976 | Samuels et al. |
| 4,014,492 A | 3/1977 | Rothfuss |
| 4,127,227 A | 11/1978 | Green |
| 4,259,959 A | 4/1981 | Walker |
| 4,263,903 A | 4/1981 | Griggs |
| 4,265,226 A | 5/1981 | Cassimally |
| 4,317,451 A | 3/1982 | Cerwin et al. |
| 4,400,833 A | 8/1983 | Kurland |
| 4,422,567 A | 12/1983 | Haynes |
| 4,454,875 A | 6/1984 | Pratt et al. |
| 4,480,641 A | 11/1984 | Failla et al. |
| 4,485,816 A | 12/1984 | Krumme |
| 4,526,174 A | 7/1985 | Froehlich |
| 4,549,545 A | 10/1985 | Levy et al. |
| 4,570,623 A | 2/1986 | Ellison et al. |
| 4,595,007 A | 6/1986 | Mericle |
| 4,624,254 A | 11/1986 | McGarry et al. |
| 4,627,437 A | 12/1986 | Bedi et al. |
| 4,632,100 A | 12/1986 | Somers et al. |
| 4,635,637 A | 1/1987 | Schreiber |
| 4,669,473 A | 6/1987 | Richards et al. |
| 4,696,300 A | 9/1987 | Anderson |
| 4,719,917 A | 1/1988 | Barrows et al. |
| 4,738,255 A | 4/1988 | Goble et al. |
| 4,741,330 A | 5/1988 | Hayhurst |
| 4,762,260 A | 8/1988 | Richards et al. |
| 4,799,495 A | 1/1989 | Hawkins et al. |
| 4,809,695 A | 3/1989 | Gwathmey et al. |
| 4,851,005 A | 7/1989 | Hunt et al. |
| 4,858,608 A | 8/1989 | McQuilkin |
| 4,884,572 A | 12/1989 | Bays et al. |
| 4,887,601 A | 12/1989 | Richards |
| 4,924,866 A | 5/1990 | Yoon |
| 4,930,674 A | 6/1990 | Barak |
| 4,968,315 A | 11/1990 | Gatturna |
| 4,976,715 A | 12/1990 | Bays et al. |
| 4,994,073 A | 2/1991 | Green |
| 4,997,436 A | 3/1991 | Oberlander |
| 5,002,536 A | 3/1991 | Thompson et al. |
| 5,013,316 A | 5/1991 | Goble et al. |
| 5,015,249 A | 5/1991 | Nakao et al. |
| 5,037,422 A | 8/1991 | Hayhurst et al. |
| 5,041,129 A | 8/1991 | Hayhurst et al. |
| 5,046,513 A | 9/1991 | Gattturna et al. |
| 5,053,047 A | 10/1991 | Yoon |
| 5,059,206 A | 10/1991 | Winters |
| 5,062,563 A | 11/1991 | Green et al. |
| 5,100,417 A | 3/1992 | Cerier et al. |
| 5,102,421 A | 4/1992 | Anspach, Jr. |
| 5,116,357 A | 5/1992 | Eberbach |
| 5,122,155 A | 6/1992 | Eberbach |
| 5,123,913 A | 6/1992 | Wilk et al. |
| RE34,021 E | 8/1992 | Mueller et al. |
| 5,141,515 A | 8/1992 | Eberbach |
| 5,141,520 A | 8/1992 | Goble et al. |
| 5,156,609 A | 10/1992 | Nakao et al. |
| 5,156,616 A | 10/1992 | Meadows et al. |
| 5,167,665 A | 12/1992 | McKinney |
| 5,171,259 A | 12/1992 | Inoue |
| 5,174,295 A | 12/1992 | Christian et al. |
| 5,174,487 A | 12/1992 | Rothfuss et al. |
| 5,176,682 A | 1/1993 | Chow |
| 5,176,692 A | 1/1993 | Wilk et al. |
| 5,203,787 A | 4/1993 | Noblitt et al. |
| 5,217,472 A | 6/1993 | Green et al. |
| 5,224,946 A | 7/1993 | Hayhurst et al. |
| 5,242,457 A | 9/1993 | Akopov et al. |
| 5,246,441 A | 9/1993 | Ross et al. |
| 5,251,642 A | 10/1993 | Handlos |
| 5,261,914 A | 11/1993 | Warren |
| 5,269,753 A | 12/1993 | Wilk |
| 5,269,783 A | 12/1993 | Sander |
| 5,282,829 A | 2/1994 | Hermes |
| 5,289,963 A | 3/1994 | McGarry et al. |
| 5,290,217 A | 3/1994 | Campos |
| 5,304,187 A | 4/1994 | Green et al. |
| 5,333,624 A | 8/1994 | Tovey |
| 5,342,396 A | 8/1994 | Cook |
| 5,350,400 A | 9/1994 | Esposito et al. |
| 5,352,229 A | 10/1994 | Goble et al. |
| 5,354,292 A | 10/1994 | Braeuer et al. |
| 5,364,408 A | 11/1994 | Gordon |
| 5,366,460 A | 11/1994 | Eberbach |
| 5,370,650 A | 12/1994 | Tovey et al. |
| 5,372,604 A | 12/1994 | Trott |
| 5,380,334 A | 1/1995 | Torrie et al. |

(56) References Cited

U.S. PATENT DOCUMENTS

| | | |
|---|---|---|
| 5,383,477 A | 1/1995 | DeMatteis |
| 5,397,332 A | 3/1995 | Kammerer et al. |
| 5,403,326 A | 4/1995 | Harrison et al. |
| 5,405,360 A | 4/1995 | Tovey |
| 5,411,522 A | 5/1995 | Trott et al. |
| 5,411,523 A | 5/1995 | Goble |
| 5,417,691 A | 5/1995 | Hayhurst |
| 5,417,712 A | 5/1995 | Whittaker et al. |
| 5,425,490 A | 6/1995 | Goble et al. |
| 5,441,502 A | 8/1995 | Bartlett |
| 5,441,508 A | 8/1995 | Gazielly et al. |
| 5,456,720 A | 10/1995 | Schultz et al. |
| 5,464,403 A | 11/1995 | Kieturakis et al. |
| 5,478,354 A | 12/1995 | Tovey et al. |
| 5,482,864 A | 1/1996 | Knobel |
| 5,486,197 A | 1/1996 | Le et al. |
| 5,497,933 A | 3/1996 | Defonzo et al. |
| 5,500,000 A | 3/1996 | Feagin et al. |
| 5,501,695 A | 3/1996 | Anspach, Jr. et al. |
| 5,503,623 A | 4/1996 | Tilton, Jr. |
| 5,505,735 A | 4/1996 | Li |
| 5,507,754 A | 4/1996 | Green et al. |
| 5,520,700 A | 5/1996 | Beyar et al. |
| 5,522,817 A | 6/1996 | Sander et al. |
| 5,545,180 A | 8/1996 | Le et al. |
| 5,560,532 A | 10/1996 | DeFonzo et al. |
| 5,562,689 A | 10/1996 | Green et al. |
| 5,569,306 A | 10/1996 | Thal |
| 5,582,616 A | 12/1996 | Bolduc et al. |
| 5,584,835 A | 12/1996 | Greenfield |
| 5,618,314 A | 4/1997 | Harwin et al. |
| 5,622,527 A | 4/1997 | Watterson et al. |
| 5,628,751 A | 5/1997 | Sander et al. |
| 5,643,319 A | 7/1997 | Green et al. |
| 5,643,321 A | 7/1997 | McDevitt |
| 5,647,874 A | 7/1997 | Hayhurst |
| 5,649,963 A | 7/1997 | McDevitt |
| 5,662,683 A | 9/1997 | Kay |
| 5,667,513 A | 9/1997 | Torrie et al. |
| 5,674,245 A | 10/1997 | Ilgen |
| 5,681,342 A | 10/1997 | Benchetrit |
| 5,702,215 A | 12/1997 | Li |
| 5,713,903 A | 2/1998 | Sander et al. |
| 5,720,753 A | 2/1998 | Sander et al. |
| 5,725,541 A | 3/1998 | Anspach, III et al. |
| 5,741,282 A | 4/1998 | Anspach, III et al. |
| 5,766,246 A | 6/1998 | Mulhauser et al. |
| 5,797,909 A | 8/1998 | Michelson |
| 5,797,931 A | 8/1998 | Bito et al. |
| 5,797,963 A | 8/1998 | McDevitt |
| 5,807,403 A | 9/1998 | Beyar et al. |
| 5,830,221 A | 11/1998 | Stein et al. |
| 5,836,961 A | 11/1998 | Kieturakis et al. |
| 5,868,762 A | 2/1999 | Cragg et al. |
| 5,873,891 A | 2/1999 | Sohn |
| 5,885,258 A | 3/1999 | Sachdeva et al. |
| 5,885,294 A | 3/1999 | Pedlick et al. |
| 5,893,856 A | 4/1999 | Jacob et al. |
| 5,904,696 A | 5/1999 | Rosenman |
| 5,919,184 A | 7/1999 | Tilton, Jr. |
| 5,922,026 A | 7/1999 | Chin |
| 5,928,244 A | 7/1999 | Tovey et al. |
| 5,948,000 A | 9/1999 | Larsen et al. |
| 5,957,939 A | 9/1999 | Heaven et al. |
| 5,957,953 A | 9/1999 | Dipoto et al. |
| 5,968,044 A | 10/1999 | Nicholson et al. |
| 5,980,557 A | 11/1999 | Iserin et al. |
| 5,989,265 A | 11/1999 | Bouquet de la Joliniere et al. |
| 5,997,552 A | 12/1999 | Person et al. |
| 6,063,088 A | 5/2000 | Winslow |
| 6,156,045 A | 12/2000 | Ulbrich et al. |
| 6,179,840 B1 | 1/2001 | Bowman |
| 6,193,731 B1 | 2/2001 | Oppelt et al. |
| 6,193,733 B1 | 2/2001 | Adams |
| 6,245,072 B1 | 6/2001 | Zdeblick et al. |
| 6,302,885 B1 | 10/2001 | Essiger |
| 6,312,442 B1 | 11/2001 | Kieturakis et al. |
| 6,315,789 B1 | 11/2001 | Cragg |
| 6,318,616 B1 | 11/2001 | Pasqualucci et al. |
| 6,322,536 B1 | 11/2001 | Rosengart et al. |
| 6,325,805 B1 | 12/2001 | Ogilvie et al. |
| 6,387,113 B1 | 5/2002 | Hawkins et al. |
| 6,391,333 B1 | 5/2002 | Li et al. |
| 6,413,274 B1 | 7/2002 | Pedros |
| 6,425,900 B1 | 7/2002 | Knodel et al. |
| 6,436,110 B2 | 8/2002 | Bowman et al. |
| 6,447,522 B2 | 9/2002 | Gambale et al. |
| 6,447,524 B1 | 9/2002 | Knodel et al. |
| 6,478,803 B1 | 11/2002 | Kapec et al. |
| 6,482,178 B1 | 11/2002 | Andrews et al. |
| 6,482,210 B1 | 11/2002 | Skiba et al. |
| 6,506,190 B1 | 1/2003 | Walshe |
| 6,511,499 B2 | 1/2003 | Schmieding et al. |
| 6,517,564 B1 | 2/2003 | Grafton et al. |
| 6,524,316 B1 | 2/2003 | Nicholson et al. |
| 6,527,795 B1 | 3/2003 | Lizardi |
| 6,530,933 B1 | 3/2003 | Yeung et al. |
| 6,540,769 B1 | 4/2003 | Miller, III |
| 6,551,333 B2 | 4/2003 | Kuhns et al. |
| 6,554,852 B1 | 4/2003 | Oberlander |
| 6,569,186 B1 | 5/2003 | Winters et al. |
| 6,575,976 B2 | 6/2003 | Grafton |
| 6,599,289 B1 | 7/2003 | Bojarski et al. |
| 6,620,185 B1 | 9/2003 | Harvie et al. |
| 6,629,988 B2 | 10/2003 | Weadock |
| 6,638,297 B1 | 10/2003 | Huiterna |
| 6,639,365 B2 | 10/2003 | Pruett |
| 6,648,893 B2 | 11/2003 | Dudasik |
| 6,666,672 B1 | 12/2003 | Steffens |
| 6,666,872 B2 | 12/2003 | Barreiro et al. |
| 6,673,094 B1 | 1/2004 | McDevitt et al. |
| 6,685,728 B2 | 2/2004 | Sinnott et al. |
| 6,692,506 B1 | 2/2004 | Ory et al. |
| 6,723,099 B1 | 4/2004 | Goshert |
| 6,726,704 B1 | 4/2004 | Loshakove et al. |
| 6,726,705 B2 | 4/2004 | Peterson et al. |
| 6,740,100 B2 | 5/2004 | Demopulos et al. |
| 6,746,472 B2 | 6/2004 | Frazier et al. |
| 6,746,500 B1 | 6/2004 | Park et al. |
| 6,770,073 B2 | 8/2004 | McDevitt et al. |
| 6,779,701 B2 | 8/2004 | Bailly et al. |
| 6,800,081 B2 | 10/2004 | Parodi |
| 6,835,206 B2 | 12/2004 | Jackson |
| 6,849,078 B2 | 2/2005 | Durgin et al. |
| 6,887,259 B2 | 5/2005 | Lizardi |
| 6,926,723 B1 | 8/2005 | Mulhauser et al. |
| 6,932,834 B2 | 8/2005 | Lizardi et al. |
| 6,946,003 B1 | 9/2005 | Wolowacz et al. |
| 6,949,117 B2 | 9/2005 | Gambale et al. |
| 6,964,685 B2 | 11/2005 | Murray et al. |
| 6,966,916 B2 | 11/2005 | Kumar |
| 6,972,027 B2 | 12/2005 | Fallin et al. |
| 6,984,241 B2 | 1/2006 | Lubbers et al. |
| 6,991,597 B2 | 1/2006 | Gellman et al. |
| 7,008,435 B2 | 3/2006 | Cummins |
| 7,021,316 B2 | 4/2006 | Leiboff |
| 7,025,772 B2 | 4/2006 | Gellman et al. |
| 7,033,379 B2 | 4/2006 | Peterson |
| 7,037,324 B2 | 5/2006 | Martinek |
| 7,048,171 B2 | 5/2006 | Thornton et al. |
| 7,063,711 B1 | 6/2006 | Loshakove et al. |
| 7,083,638 B2 | 8/2006 | Foerster |
| 7,087,064 B1 | 8/2006 | Hyde |
| 7,122,214 B2 | 10/2006 | Xie |
| 7,144,403 B2 | 12/2006 | Booth |
| 7,144,414 B2 | 12/2006 | Harvie et al. |
| 7,150,750 B2 | 12/2006 | Damarati |
| 7,153,314 B2 | 12/2006 | Laufer et al. |
| 7,160,314 B2 | 1/2007 | Sgro et al. |
| 7,160,326 B2 | 1/2007 | Ball |
| 7,163,536 B2 | 1/2007 | Godara |
| 7,163,551 B2 | 1/2007 | Anthony et al. |
| 7,169,157 B2 | 1/2007 | Kayan |
| 7,188,581 B1 | 3/2007 | Davis et al. |

(56) References Cited

U.S. PATENT DOCUMENTS

| | | |
|---|---|---|
| 7,189,251 B2 | 3/2007 | Kay |
| 7,201,754 B2 | 4/2007 | Stewart et al. |
| 7,214,232 B2 | 5/2007 | Bowman et al. |
| 7,226,469 B2 | 6/2007 | Benavitz et al. |
| 7,229,452 B2 | 6/2007 | Kayan |
| 7,247,164 B1 | 7/2007 | Ritchart et al. |
| 7,303,557 B2 | 12/2007 | Wham et al. |
| 7,306,337 B2 | 12/2007 | Ji et al. |
| 7,320,692 B1 | 1/2008 | Bender et al. |
| 7,320,701 B2 | 1/2008 | Haut et al. |
| 7,322,935 B2 | 1/2008 | Palmer et al. |
| 7,326,231 B2 | 2/2008 | Phillips et al. |
| 7,343,920 B2 | 3/2008 | Toby et al. |
| 7,368,124 B2 | 5/2008 | Chun et al. |
| 7,377,934 B2 | 5/2008 | Lin et al. |
| 7,381,213 B2 | 6/2008 | Lizardi |
| 7,390,329 B2 | 6/2008 | Westra et al. |
| 7,399,304 B2 | 7/2008 | Gambale et al. |
| 7,404,824 B1 | 7/2008 | Webler et al. |
| 7,416,554 B2 | 8/2008 | Lam et al. |
| 7,452,368 B2 | 11/2008 | Liberatore et al. |
| 7,460,913 B2 | 12/2008 | Kuzma et al. |
| 7,463,933 B2 | 12/2008 | Wahlstrom et al. |
| 7,465,308 B2 | 12/2008 | Sikora et al. |
| 7,481,832 B1 | 1/2009 | Meridew et al. |
| 7,485,124 B2 | 2/2009 | Kuhns et al. |
| 7,497,584 B1 | 3/2009 | Quittner |
| 7,500,972 B2 | 3/2009 | Voegele et al. |
| 7,500,980 B2 | 3/2009 | Gill et al. |
| 7,500,983 B1 | 3/2009 | Kaiser et al. |
| 7,503,474 B2 | 3/2009 | Hillstead et al. |
| 7,506,791 B2 | 3/2009 | Omaits et al. |
| 7,559,941 B2 | 7/2009 | Zannis et al. |
| 7,572,276 B2 | 8/2009 | Lim et al. |
| 7,585,311 B2 | 9/2009 | Green et al. |
| 7,766,208 B2 | 8/2010 | Epperly et al. |
| 7,771,440 B2 | 8/2010 | Ortiz et al. |
| 7,776,057 B2 | 8/2010 | Laufer et al. |
| 7,780,685 B2 | 8/2010 | Hunt et al. |
| 7,785,255 B2 | 8/2010 | Malkani |
| 7,807,192 B2 | 10/2010 | Li et al. |
| 7,819,880 B2 | 10/2010 | Zannis et al. |
| 7,918,879 B2 | 4/2011 | Yeung et al. |
| 8,114,101 B2 | 2/2012 | Criscuolo et al. |
| 8,197,837 B2 | 6/2012 | Jamiolkowski et al. |
| 8,585,773 B1 | 11/2013 | Kucklick |
| 9,878,141 B2 | 1/2018 | Kucklick |
| 2002/0077687 A1 | 6/2002 | Ahn |
| 2002/0090725 A1 | 7/2002 | Simpson et al. |
| 2002/0123767 A1 | 9/2002 | Prestel |
| 2002/0165559 A1 | 11/2002 | Grant et al. |
| 2003/0073979 A1 | 4/2003 | Naimark et al. |
| 2003/0125748 A1 | 7/2003 | Li et al. |
| 2003/0212456 A1 | 11/2003 | Lipchitz et al. |
| 2004/0059416 A1 | 3/2004 | Murray et al. |
| 2004/0138705 A1 | 7/2004 | Heino et al. |
| 2004/0167519 A1 | 8/2004 | Weiner et al. |
| 2004/0267277 A1* | 12/2004 | Zannis .............. A61F 2/4618  606/99 |
| 2005/0015021 A1 | 1/2005 | Shiber |
| 2005/0049618 A1 | 3/2005 | Masuda et al. |
| 2005/0051597 A1 | 3/2005 | Toledano |
| 2005/0059996 A1 | 3/2005 | Bauman et al. |
| 2005/0060033 A1 | 3/2005 | Vacanti et al. |
| 2005/0107807 A1 | 5/2005 | Nakao |
| 2005/0113736 A1 | 5/2005 | Orr et al. |
| 2005/0171569 A1 | 8/2005 | Girard et al. |
| 2005/0187576 A1 | 8/2005 | Whitman et al. |
| 2005/0240222 A1 | 10/2005 | Shipp |
| 2005/0274768 A1 | 12/2005 | Cummins et al. |
| 2006/0074423 A1 | 4/2006 | Alleyne et al. |
| 2006/0178743 A1 | 8/2006 | Carter |
| 2006/0235442 A1 | 10/2006 | Huitema |
| 2006/0293760 A1 | 12/2006 | DeDeyne |
| 2007/0078477 A1 | 4/2007 | Heneveld et al. |
| 2007/0083236 A1 | 4/2007 | Sikora et al. |
| 2007/0112361 A1 | 5/2007 | Schonholz et al. |
| 2007/0179531 A1 | 8/2007 | Thornes |
| 2007/0185506 A1 | 8/2007 | Jackson |
| 2007/0190108 A1 | 8/2007 | Datta et al. |
| 2007/0219558 A1 | 9/2007 | Deutsch |
| 2007/0270804 A1 | 11/2007 | Chudik |
| 2007/0288023 A1 | 12/2007 | Pellegrino et al. |
| 2008/0027470 A1 | 1/2008 | Hart et al. |
| 2008/0051888 A1 | 2/2008 | Ratcliffe et al. |
| 2008/0065153 A1 | 3/2008 | Allard et al. |
| 2008/0090936 A1 | 4/2008 | Fujimura et al. |
| 2008/0125869 A1 | 5/2008 | Paz et al. |
| 2008/0135600 A1 | 6/2008 | Hiranuma et al. |
| 2008/0173691 A1 | 7/2008 | Mas et al. |
| 2008/0188874 A1 | 8/2008 | Henderson |
| 2008/0188936 A1 | 8/2008 | Ball et al. |
| 2008/0195119 A1 | 8/2008 | Ferree |
| 2008/0200949 A1 | 8/2008 | Hiles et al. |
| 2008/0241213 A1 | 10/2008 | Chun et al. |
| 2008/0272173 A1 | 11/2008 | Coleman et al. |
| 2008/0306408 A1 | 12/2008 | Lo |
| 2009/0001122 A1 | 1/2009 | Prommersberger et al. |
| 2009/0012521 A1 | 1/2009 | Axelson, Jr. et al. |
| 2009/0030434 A1 | 1/2009 | Paz et al. |
| 2009/0069806 A1 | 3/2009 | De La Mora Levy et al. |
| 2009/0076541 A1 | 3/2009 | Chin et al. |
| 2009/0105535 A1 | 4/2009 | Green et al. |
| 2009/0112085 A1 | 4/2009 | Eby |
| 2009/0134198 A1 | 5/2009 | Knodel et al. |
| 2009/0156986 A1 | 6/2009 | Trenhaile |
| 2009/0156997 A1 | 6/2009 | Trenhaile |
| 2009/0182245 A1 | 7/2009 | Zambelli |
| 2009/0242609 A1 | 10/2009 | Kanner |
| 2010/0145367 A1 | 6/2010 | Ratcliffe |
| 2010/0147922 A1 | 6/2010 | Olson |
| 2010/0163598 A1 | 7/2010 | Belzer |
| 2010/0191332 A1 | 7/2010 | Euteneuer et al. |
| 2010/0241227 A1 | 9/2010 | Euteneuer et al. |
| 2010/0249801 A1 | 9/2010 | Sengun et al. |
| 2010/0256675 A1 | 10/2010 | Romans |
| 2010/0274278 A1 | 10/2010 | Fleenor et al. |
| 2010/0292715 A1 | 11/2010 | Nering et al. |
| 2010/0292791 A1 | 11/2010 | Lu et al. |
| 2010/0312250 A1 | 12/2010 | Euteneuer et al. |
| 2010/0312275 A1 | 12/2010 | Euteneuer et al. |
| 2010/0312357 A1* | 12/2010 | Levin .............. A61B 17/064  623/23.72 |
| 2010/0327042 A1 | 12/2010 | Amid et al. |
| 2011/0000950 A1 | 1/2011 | Euteneuer et al. |
| 2011/0004221 A1 | 1/2011 | Euteneuer et al. |
| 2011/0011917 A1 | 1/2011 | Loulmet |
| 2011/0034942 A1 | 2/2011 | Levin et al. |
| 2011/0040310 A1 | 2/2011 | Levin et al. |
| 2011/0040311 A1 | 2/2011 | Levin et al. |
| 2011/0066166 A1 | 3/2011 | Levin et al. |
| 2011/0106154 A1 | 5/2011 | DiMatteo et al. |
| 2011/0114700 A1 | 5/2011 | Baxter, III et al. |
| 2011/0224702 A1 | 9/2011 | Van Kampen et al. |
| 2011/0264149 A1 | 10/2011 | Pappalardo et al. |
| 2012/0100200 A1 | 4/2012 | Belcheva et al. |
| 2012/0160893 A1 | 6/2012 | Harris et al. |
| 2012/0193391 A1 | 8/2012 | Michler et al. |
| 2012/0248171 A1 | 10/2012 | Bailly et al. |
| 2012/0316608 A1 | 12/2012 | Foley |
| 2016/0256254 A1 | 9/2016 | Kucklick |
| 2016/0262780 A1 | 9/2016 | Kucklick |

FOREIGN PATENT DOCUMENTS

| | | |
|---|---|---|
| EP | 0298400A1 A1 | 1/1989 |
| EP | 0390613 A1 | 10/1990 |
| EP | 0543499 A1 | 5/1993 |
| EP | 0548998 A1 | 6/1993 |
| EP | 0557963 A1 | 9/1993 |
| EP | 0589306 A2 | 3/1994 |
| EP | 0908152 A1 | 4/1999 |
| EP | 1491157 A1 | 12/2004 |
| EP | 1559379 A1 | 8/2005 |

(56) References Cited

FOREIGN PATENT DOCUMENTS

| EP | 2030576 | A2 | 3/2009 |
|---|---|---|---|
| GB | 2154688 | A | 9/1985 |
| GB | 2397240 | A | 7/2004 |
| JP | 58188442 | | 11/1983 |
| JP | 2005506122 | | 3/2005 |
| JP | 2006515774 | | 6/2006 |
| WO | 85005025 | | 11/1985 |
| WO | 0176456 | A2 | 10/2001 |
| WO | 200234140 | A2 | 5/2002 |
| WO | 2003105670 | A2 | 12/2003 |
| WO | 2004000138 | A1 | 12/2003 |
| WO | 2004093690 | A1 | 11/2004 |
| WO | 2005016389 | A2 | 2/2005 |
| WO | 2006086679 | A1 | 8/2006 |
| WO | 2007014910 | A1 | 2/2007 |
| WO | 2007030676 | A2 | 3/2007 |
| WO | 2007078978 | A2 | 7/2007 |
| WO | 2007082088 | A2 | 7/2007 |
| WO | 2008111073 | A2 | 9/2008 |
| WO | 2008111078 | A2 | 9/2008 |
| WO | 2008139473 | A2 | 11/2008 |
| WO | 2009079211 | A1 | 6/2009 |
| WO | 2009143331 | A1 | 11/2009 |
| WO | 2011095890 | A2 | 8/2011 |
| WO | 2011128903 | A2 | 10/2011 |
| WO | 2018144887 | A1 | 8/2018 |

OTHER PUBLICATIONS

Euteneuer et al.; U.S. Appl. No. 13/889,687 entitled "Methods and Apparatus for Delivering Staples to a Target Tissue," filed May 8, 2013.
Euteneuer et al.; U.S. Appl. No. 13/889,722 entitled "Apparatus and Method for Forming Pilot Holes in Bone and Delivering Fasteners Therein for Retaining an Implant," filed May 8, 2013.
Euteneuer et al.; U.S. Appl. No. 13/889,737 entitled "Fasteners and Fastener Delivery Devices for Affixing Sheet-Like Materials To Bone or Tissue," filed May 8, 2013.
Euteneuer et al.; U.S. Appl. No. 13/889,757 entitled "Methods and Apparatus for Delivering and Positioning Sheet-Like Materials in Surgery," filed May 8, 2013.
Euteneuer et al.; U.S. Appl. No. 13/889,774 entitled "Guidewire Having a Distal Fixation Member for Delivering and Positioning Sheet-Like Materials in Surgery," filed May 8, 2013.
Euteneuer et al.; U.S. Appl. No. 13/889,832 entitled "Anatomical location Markers and Methods of Use in Positioning Sheet-Like Materials During Surgery," filed May 8, 2013.
Van Kampen et al.; U.S. Appl. No. 13/889,701 entitled "Tendon repair implant and method of arthroscopic implantation," filed May 8, 2013.
Stetson et al.; Arthroscopic treatment of partial rotator cuff tears; Operative Techniques in Sports Medicine; vol. 12, Issue 2; pp. 135-148; Apr. 2004.
Wikipedia, the free encyclopedia; Rotator cuff tear; downloaded from <http://en.wikipedia.org/wiki/Rotator_cuff_tear> on Dec. 6, 2012; 14 pages.
Euteneuer et al.; U.S. Appl. No. 13/717,474 entitled "Apparatus and Method for Forming Pilot Holes in Bone and Delivering Fasteners Therein for Retaining An Implant," filed Dec. 17, 2012.
Euteneuer et al.; U.S. Appl. No. 13/717,493 entitled "Fasteners and Fastener Delivery Devices for Affixing Sheet-Like Materials to Bone or Tissue," filed Dec. 17, 2012.
Euteneuer et al.; U.S. Appl. No. 13/717,515 entitled "Fasteners and Fastener Delivery Devices for Affixing Sheet-Like Materials to Bone or Tissue," filed Dec. 17, 2012.
Euteneuer et al.; U.S. Appl. No. 13/717,530 entitled Fasteners and Fastener Delivery Devices for Affixing Sheet-Like Materials to Bone or Tissue, filed Dec. 17, 2012.
Euteneuer et al.; U.S. Appl. No. 13/722,796 entitled "Methods and Apparatus for Delivering and Positioning Sheet-Like Materials in Surgery," filed Dec. 20, 2012.
Euteneuer et al.; U.S. Appl. No. 13/722,865 entitled "Guidewire Having a Distal Fixation Member for Delivering and Positioning Sheet-Like Materials in Surgery," filed Dec. 20, 2012.
Euteneuer et al.; U.S. Appl. No. 13/722,940 entitled "Anatomical Location Markers and Methods of Use in Positioning Sheet-Like Materials During Surgery," filed Dec. 20, 2012.
Euteneuer et al.; U.S. Appl. No. 13/763,414 entitled "Implantable Tendon Protection Systems and Related Kits and Methods," filed Feb. 8, 2013.
Alexander et al.; Ligament and tendon repair with an absorbable polymer-coated carbon fiber stend; Bulletin of the Hospital for Join Diseases Orthopaedic Institute; vol. 46; No. 2; pp. 155-173; Fall 1986.
Bahler et al.; Trabecular bypass stents decrease intraocular pressure in cultured himan anterior segments; Am. J. Ophthalmology; vol. 138; No. 6; pp. 988-994; Dec. 2004.
Charnay et al.; Digital contracture deformity after implantation of a silicone prothesis: Light and electron study; The Journal of Hand Surgery; vol. 3; No. 3; pp. 266-270; May 1978.
D'Ermo et al.; Our results with the operation of ab externo; Ophthalmologica; vol. 168; pp. 347-355; (month unavailable) 1971.
France et al.; Biomechanical evaluation of rotator cuff fixation methods; The American Journal of Sports Medicine; vol. 17; No. 2; Mar.-Apr. 1989.
Goodship et al.; An assessment of filamentous carbon fibre for the treatment of tendon injury in the horse; Veterinary record; vol. 106; pp. 217-221; Mar. 8, 1980.
Hunter et al.; Flexor-tendon reconstruction in severely damaged hands; The Journal of Bone and Joint Surgery (American Volume); vol. 53-A; No. 5; pp. 329-358; Jul. 1971.
Johnstone et al.; Microsurgery of Schlemm's canal and the human aqueous outflow system; Am J. Ophthalmology; vol. 79; No. 6; pp. 906-917; Dec. 1973.
Kowalsky et al.; Evaluation of suture abrasion against rotator cuff tendon and proximal humerus bone; Arthroscopy: The Journal of Arthroscopic and Related Surgery; vol. 24; No. 3; pp. 329-334; Mar. 2008.
Lee et al.; Aqueous-venous an intaocular pressure. Preliminary report of animal studies; Investigative Ophthalmology; vol. 5; No. 1; pp. 59-64; Feb. 1966.
Maepea et al.; The pressures in the episcleral veins, Schlemm's canal and the trabecular meshwork in monkeys: Effects of changes in intraocular pressure; Exp. Eye Res.; vol. 49; pp. 645-663; Oct. 1989.
Nicolle et al.; A silastic tendon prosthesis as an adjunct to flexor tendon grafting: An experimental and clinical evaluation; British Journal of Plastic Surgery; vol. 22; Issues 3-4; pp. 224-236; (month unavailable) 1969.
Rubin et al.; The use of acellular biologic tissue patches in foot and ankle surgery; Clinics in Podiatric Medicine and Surgery; vol. 22; pp. 533-552; Oct 2005.
Schultz: Canaloplasty procedure shows promise for open-angle glaucoma in European study; Ocular Surgery News; pp. 34-35; Mar. 1, 2007.
Spiegel et al.; Schlemm's canal implant: A new method to lower intraocular pressure in patients with POAG; Ophthalmic Surgery and Lasers; vol. 30; No. 6; pp. 492-494; Jun. 1999.
Valdez et al.; Repair of digital flexor tendon lacerations in the horse, using carbon fiber implants; JAYMA; vol. 177; No. 5; pp. 427-435; Sep. 1, 1980.
Euteneuer, Charles L.; U.S. Appl. No. 13/397,573 entitled "Methods and Apparatus for Fixing Sheet-Like Materials to a Target Tissue." filed Feb. 15, 2012.

* cited by examiner

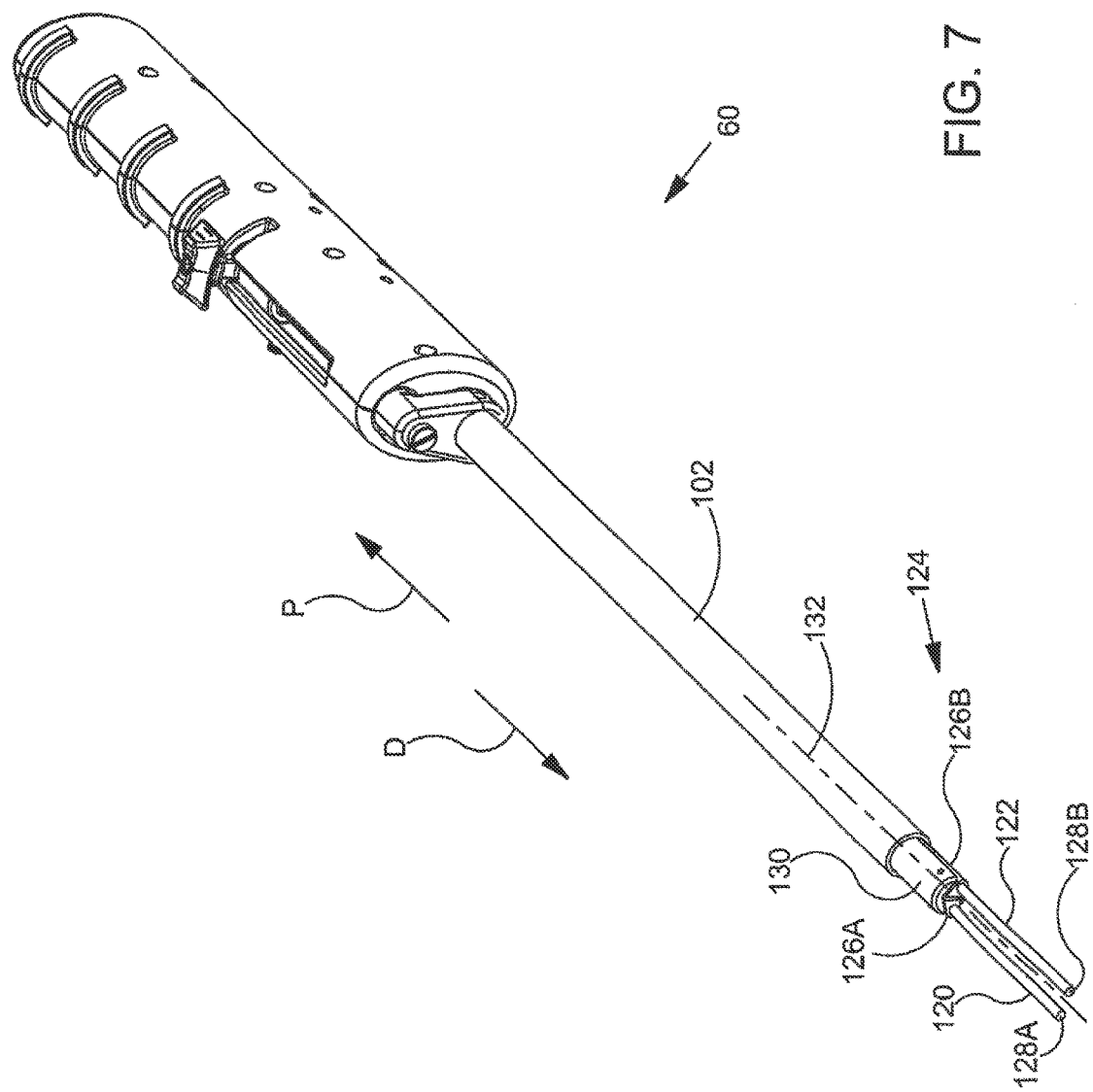

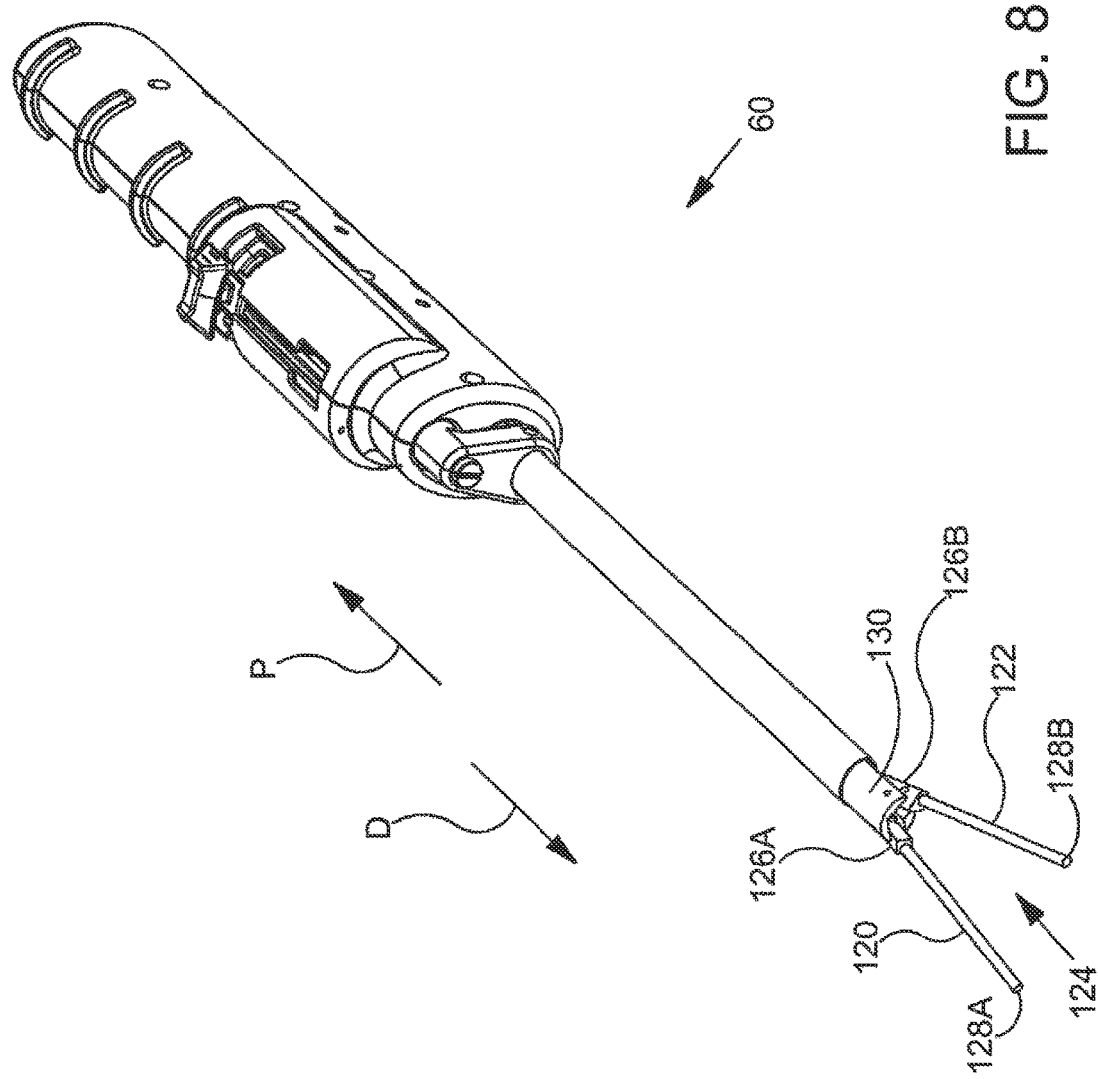

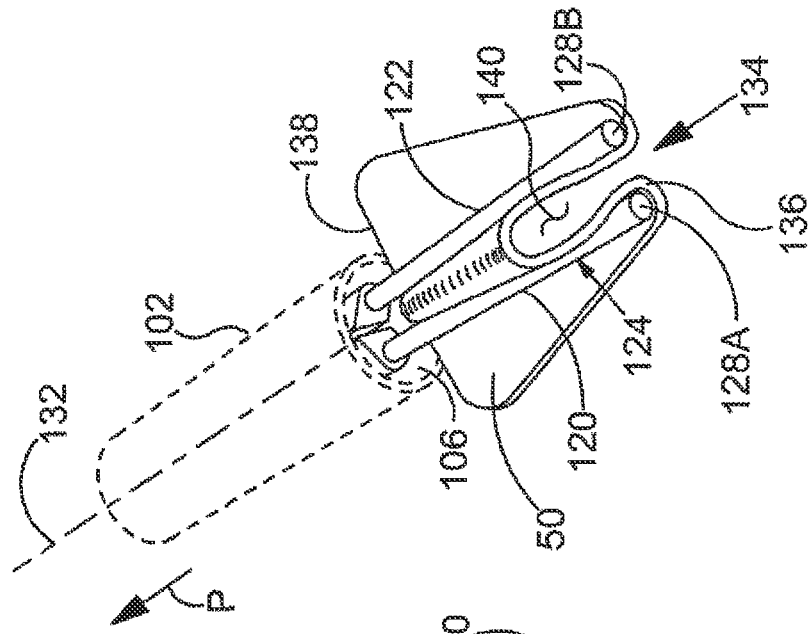
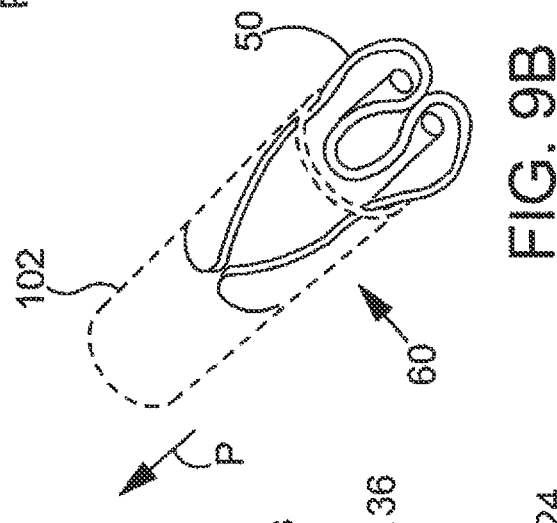
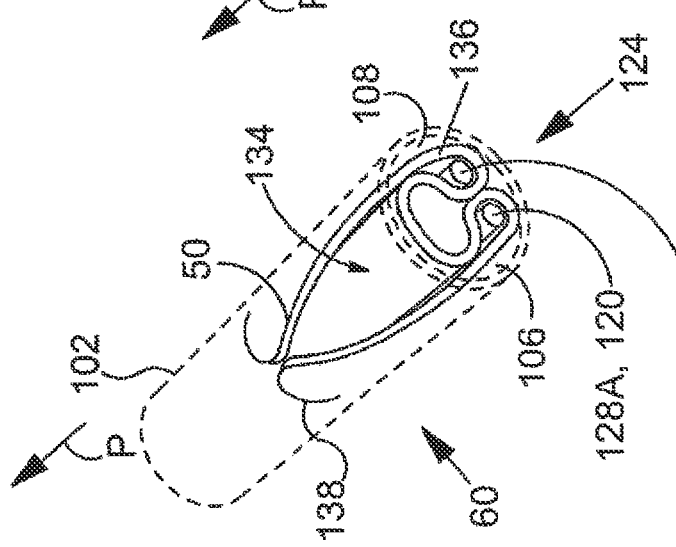

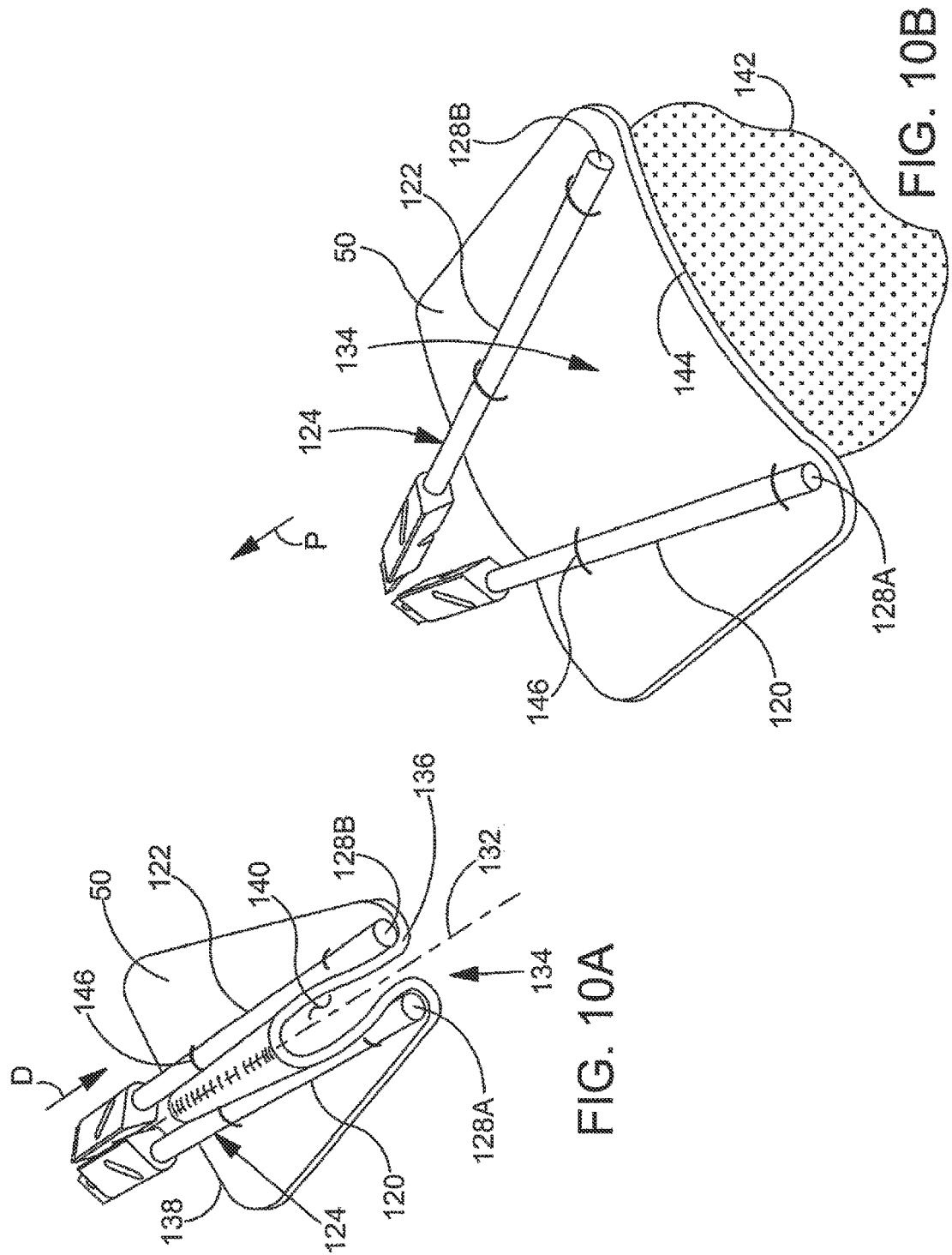

METHODS AND APPARATUS FOR DELIVERING AND POSITIONING SHEET-LIKE MATERIALS

CROSS REFERENCE TO RELATED APPLICATIONS

This application is a continuation of U.S. application Ser. No. 14/506,029, filed on Oct. 3, 2014, which is a continuation of U.S. application Ser. No. 13/397,603, filed on Feb. 15, 2012, now U.S. Pat. No. 8,864,780, which claims the benefit of U.S. Provisional Application No. 61/443,169, filed on Feb. 15, 2011.

FIELD

The present invention relates generally to orthopedic medicine and surgery. More particularly, the present invention relates to methods and apparatus for delivery and fixation of sheet-like implants, such as for treating articulating joints.

BACKGROUND

The glenohumeral joint of the shoulder is found where the head of the humerus mates with a shallow depression in the scapula. This shallow depression is known as the glenoid fossa. Six muscles extend between the humerus and scapula and actuate the glenohumeral joint. These six muscles include the deltoid, the teres major, and the four rotator cuff muscles. As disclosed by Ball et al. in U.S. Patent Publication No. U.S. 2008/0188936 A1 and as illustrated in FIG. 1 the rotator cuff muscles are a complex of muscles. The muscles of the rotator cuff include the supraspinatus, the infraspinatus, the subscapularis, and the teres minor. The centering and stabilizing roles played by the rotator cuff muscles are critical to the proper function of the shoulder. The rotator cuff muscles provide a wide variety of moments to rotate the humerus and to oppose unwanted components of the deltoid and pectoralis muscle forces.

The muscles of the rotator cuff arise from the scapula 12. The distal tendons of the rotator cuff muscles splay out and interdigitate to form a common continuous insertion on the humerus 14. The subscapularis 16 arises from the anterior aspect of the scapula 12 and attaches over much of the lesser tuberosity of the humerus. The supraspinatus muscle 18 arises from the supraspinatus fossa of the posterior scapula, passes beneath the acromion and the acromioclavicular joint, and attaches to the superior aspect of the greater tuberosity 11. The infraspinatus muscle 13 arises from the infraspinous fossa of the posterior scapula and attaches to the posterolateral aspect of the greater tuberosity 11. The teres minor 15 arises from the lower lateral aspect of the scapula 12 and attaches to the lower aspect of the greater tuberosity 11.

The mechanics of the rotator cuff muscles 10 are complex. The rotator cuff muscles 10 rotate the humerus 14 with respect to the scapula 12, compress the humeral head 17 into the glenoid fossa providing a critical stabilizing mechanism to the shoulder (known as concavity compression), and provide muscular balance. The supraspinatus and infraspinatus provide 45 percent of abduction and 90 percent of external rotation strength. The supraspinatus and deltoid muscles are equally responsible for producing torque about the shoulder joint in the functional planes of motion.

The rotator cuff muscles 10 are critical elements of this shoulder muscle balance equation. The human shoulder has no fixed axis. In a specified position, activation of a muscle creates a unique set of rotational moments. For example, the anterior deltoid can exert moments in forward elevation, internal rotation, and cross-body movement. If forward elevation is to occur without rotation, the cross-body and internal rotation moments of this muscle must be neutralized by other muscles, such as the posterior deltoid and infraspinatus. The timing and magnitude of these balancing muscle effects must be precisely coordinated to avoid unwanted directions of humeral motion. Thus the simplified view of muscles as isolated motors, or as members of force couples must give way to an understanding that all shoulder muscles function together in a precisely coordinated way—opposing muscles canceling out undesired elements leaving only the net torque necessary to produce the desired action. Injury to any of these soft tissues can greatly inhibit ranges and types of motion of the arm.

With its complexity, range of motion and extensive use, a fairly common soft tissue injury is damage to the rotator cuff or rotator cuff tendons. Damage to the rotator cuff is a potentially serious medical condition that may occur during hyperextension, from an acute traumatic tear or from overuse of the joint. With its critical role in abduction, rotational strength and torque production, the most common injury associated with the rotator cuff region is a strain or tear involving the supraspinatus tendon. A tear in the supraspinitus tendon 19 is schematically depicted in FIG. 2. A tear at the insertion site of the tendon with the humerus, may result in the detachment of the tendon from the bone. This detachment may be partial or full, depending upon the severity of the injury. Additionally, the strain or tear can occur within the tendon itself. Injuries to the supraspinatus tendon 19 and recognized modalities for treatment are defined by the type and degree of tear. The first type of tear is a full thickness tear as also depicted in FIG. 2, which as the term indicates is a tear that extends through the thickness of the supraspinatus tendon regardless of whether it is completely torn laterally. The second type of tear is a partial thickness tear which is further classified based on how much of the thickness is torn, whether it is greater or less than 50% of the thickness.

The accepted treatment for a full thickness tear or a partial thickness tear greater than 50% includes reconnecting the torn tendon via sutures. For the partial thickness tears greater than 50%, the tear is completed to a full thickness tear by cutting the tendon prior to reconnection. In contrast to the treatment of a full thickness tear or a partial thickness tear of greater than 50%, the treatment for a partial thickness tear less than 50% usually involves physical cessation from use of the tendon, i.e., rest. Specific exercises can also be prescribed to strengthen and loosen the shoulder area. In many instances, the shoulder does not heal and the partial thickness tear can be the source of chronic pain and stiffness. Further, the pain and stiffness may cause restricted use of the limb which tends to result in further degeneration or atrophy in the shoulder. Surgical intervention may be required for a partial thickness tear of less than 50%, however, current treatment interventions do not include repair of the tendon, rather the surgical procedure is directed to arthroscopic removal of bone to relieve points of impingement or create a larger tunnel between the tendon and bone that is believed to be causing tendon damage. As part of the treatment, degenerated tendon may also be removed using a debridement procedure in which tendon material is ablated. Again, the tendon partial tear is not repaired. Several authors have reported satisfactory early post operative results from these procedures, but over time recurrent symptoms have been noted. In the event of recurrent symptoms, many times a patient will "live with the pain". This may result in less use of the arm and shoulder which causes further degeneration of the tendon and may lead to more extensive damage. A tendon repair would then need to be done in a later procedure if the prescribed treatment for partial tear was unsuccessful in relieving pain and stiffness or over time the tear propagated through injury or degeneration to a full thickness tear or a partial thickness tear greater than 50% with attendant pain and debilitation. A subsequent later procedure would include the more drastic procedure of completing the tear to full thickness and suturing the ends of the tendon back together. This procedure requires extensive rehabilitation, has relatively high failure rates and subjects the patient who first presented and was treated with a partial thickness tear less than 50% to a second surgical procedure.

As described above, adequate treatments do not currently exist for repairing a partial thickness tear of less than 50% in the supraspinatus tendon. Current procedures attempt to alleviate impingement or make room for movement of the tendon to prevent further damage and relieve discomfort but do not repair or strengthen the tendon. Use of the still damaged tendon can lead to further damage or injury. Prior damage may result in degeneration that requires a second more drastic procedure to repair the tendon. Further, if the prior procedure was only partially successful in relieving pain and discomfort, a response may be to use the shoulder less which leads to degeneration and increased likelihood of further injury along with the need for more drastic surgery. There is a large need for surgical techniques and systems to treat partial thickness tears of less than 50% and prevent future tendon damage by strengthening or repairing the native tendon having the partial thickness tear.

SUMMARY OF THE DISCLOSURE

The disclosure is directed to an implant delivery system for delivering a sheet-like implant. One embodiment provides an implant delivery system including an implant retainer assembly and an implant spreader assembly. The implant retainer assembly and the implant spreader are provided proximate the distal end of a delivery shaft. The implant retainer assembly is configured to releasably couple a sheet-like implant thereto for positioning the sheet-like implant at a treatment site. The implant spreader assembly is configured to expand the sheet-like implant so that the sheet-like implant covers the treatment site.

In some exemplary embodiments, the implant spreader assembly includes a first arm and a second arm each having a proximal and a distal end. The proximal end of each arm is pivotably connected proximate the distal end of the delivery shaft. The first and second arms are moveable between a closed position and an open position. When the first and second arms are in the closed position, the arms extend generally in the longitudinal direction. When pivoting to the open position the distal end of each arm travels in a generally transverse direction to spread an implant positioned on the implant retainer assembly. When pivoting from the open position to the closed position, the first arm and the second arm may travel in different planes.

In some exemplary embodiments, a sheath is disposed about the implant spreader assembly. The sheath is slidable in a direction generally parallel to a longitudinal axis of the delivery shaft such that the sheath can be retracted proximally from around the implant spreader assembly. The sheath can include a bullet nose distal end to ease insertion into the shoulder space. A sheet-like implant may be releasably coupled to the implant retainer assembly. When this is the case, the sheet-like implant may fit within the sheath when the implant spreader is in the closed position. The sheet-like implant may then be expanded to cover a treatment site when the sheath is retracted and the implant spreader is opened. In some useful embodiments, the sheet-like implant extends tautly between the arms of the implant spreader when the arms are in the open position. The sheet-like implant may assume a rolled configuration when the implant expander is in the closed position.

In some exemplary embodiments, the first arm and the second arm pivot transversely in different planes such that in the open position the sheet-like implant extending between the arms forms a generally curved surface to conform to a generally curved treatment site when placed thereon. In some instances, the first arm and the second arm pivot transversely in the same plane such that in the open position the sheet-like implant extending between the arms forms a generally flat surface.

In some embodiments, the implant retainer assembly comprises a center post disposed proximate the distal end of the delivery shaft. A plurality of spikes may be provided on the center post. The spikes may be configured to releasably couple a sheet-like implant to the center post for positioning the sheet-like implant at a treatment site. The center post may also include, for instance, a first finger and a second finger defining a slot that is dimensioned to receive the sheet-like implant. Either finger or both fingers may be moveable in a axial direction (distally or proximally) to aid in releasing a sheet-like implant. The fingers could also be moveable in that they could rotate in either in the same direction or in opposite directions around an axis at their proximal ends in order to release the sheet-like implant.

Another embodiment provides an implant delivery system including a delivery shaft having a proximal end and a distal end defining a generally longitudinal direction. An implant spreader assembly is provided proximate the distal end of the delivery shaft. A sheet-like implant is coupled to the implant spreader such that the implant is folded when the arms of the implant spreader are in a closed position and unfolded when the arms of the implant spreader are in an open position. The implant spreader assembly may be used to unfold the sheet-like implant, for example, to spread the implant over a treatment site within the body. In some embodiments, the implant defines a trough having a depth that varies between a proximal edge of the implant and a distal edge of the implant when the implant expander is in the closed position.

In some exemplary embodiments, the implant spreader assembly includes a first arm and a second arm each having a proximal and a distal end. The proximal end of each arm is pivotably connected proximate the distal end of the delivery shaft. The first and second arms are moveable between the closed position and the open position. When the first and second arms are in the closed position, the arms extend generally in the longitudinal direction. When pivoting to the open position the distal end of each arm travels in a generally transverse direction to spread a sheet-like implant. When pivoting from the open position to the closed position, the first arm and the second arm may travel in different planes.

In some exemplary embodiments, a sheath is disposed about the implant spreader assembly. The sheath is slidable in a direction generally parallel to a longitudinal axis of the delivery shaft such that the sheath can be retracted proximally from around the implant spreader assembly. A sheet-like implant may be releasably coupled to the arms. When this is the case, the sheet-like implant may fit within the sheath when the implant spreader is in the closed position. The sheet-like implant may assume a rolled or folded configuration when the implant expander is in the closed position and the implant is disposed within the lumen defined by the sheath. In some embodiments, the implant is arranged within the sheath such that a distal edge of the implant substantially corresponds to an upper case omega in the Greek alphabet. The implant may also be arranged within the sheath such that a distal edge of the implant substantially corresponds to a lower case omega in the Greek alphabet in some embodiments.

A method of treating a rotator cuff of a shoulder may include the step of providing an implant delivery system as described above. A shoulder of the patient may be inflated to create cavity therein. An introducer cannula can be used to provide a means for inserting the implant delivery device. The implant and the implant spreader assembly may be placed inside the cavity. The implant may be spread over a target tissue at the treatment site. The implant may be affixed to the target tissue. The implant may be released from the implant delivery system. The implant spreader assembly may be removed from the cavity. In some cases, the implant spreader assembly is assuming the closed configuration while the implant spreader assembly is withdrawn from the cavity.

BRIEF DESCRIPTION OF THE DRAWINGS

FIG. 7 is an additional perspective view further illustrating the implant delivery system shown in the previous figure;

FIG. 8 is an additional perspective view further illustrating the implant delivery system shown in the previous figure;

FIG. 9A through FIG. 9C are a series of stylized perspective views illustrating at least part of an exemplary method in accordance with the present detailed description. This method may be used, for example, to deliver a sheet-like implant into the human body while the implant is arranged to fit within a relatively compact volume defined by a sheath. This exemplary process may also be used to expand the implant to cover and/or place the implant proximal to a treatment site within the body;

FIG. 10A and FIG. 10B are a pair of stylized perspective views illustrating the open and closed positions that may be assumed by a first arm and a second arm of an implant spreader assembly in accordance with the detailed description;

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

Figure 1:
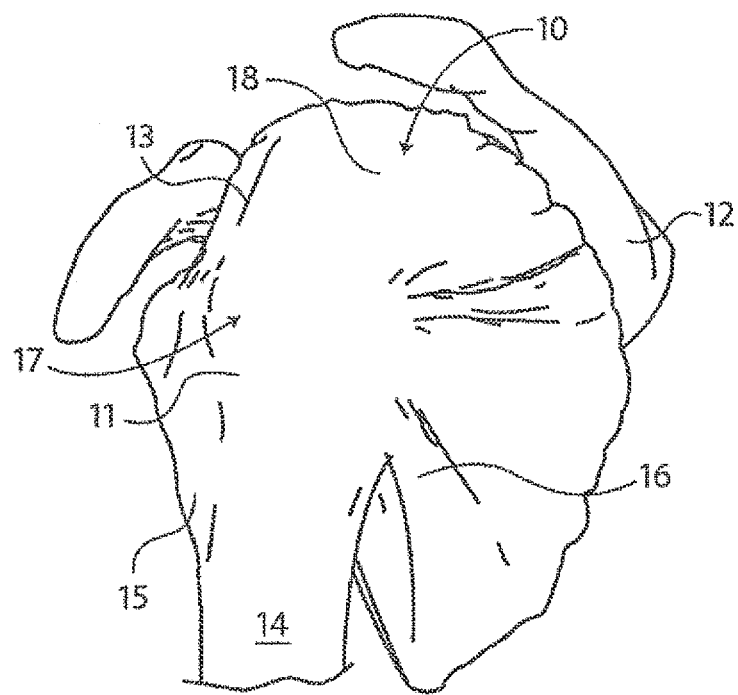
FIG. 1 is a simplified perspective view of the human rotator cuff and associated anatomical structure.
Figure 2:
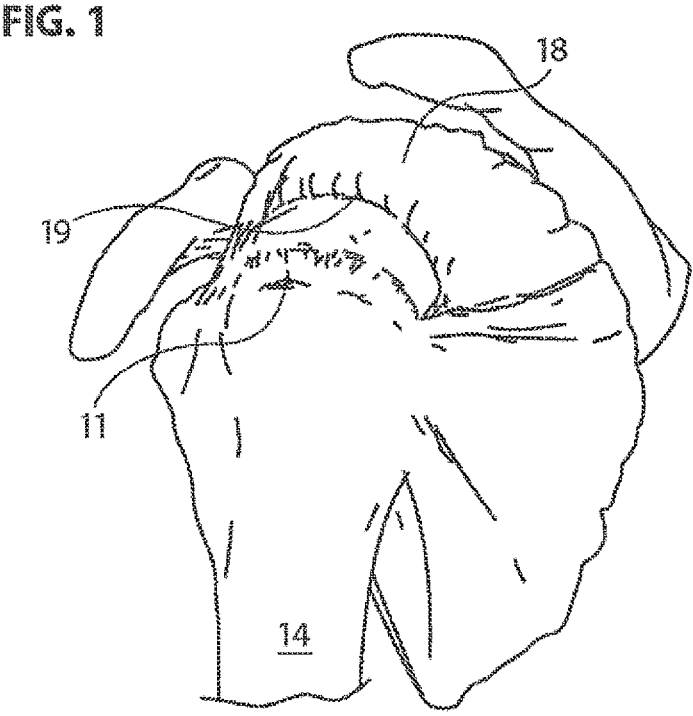
FIG. 2 is a schematic depiction of a full thickness tear in the supraspinatus tendon of the rotator cuff of FIG. 1.
Figure 3:
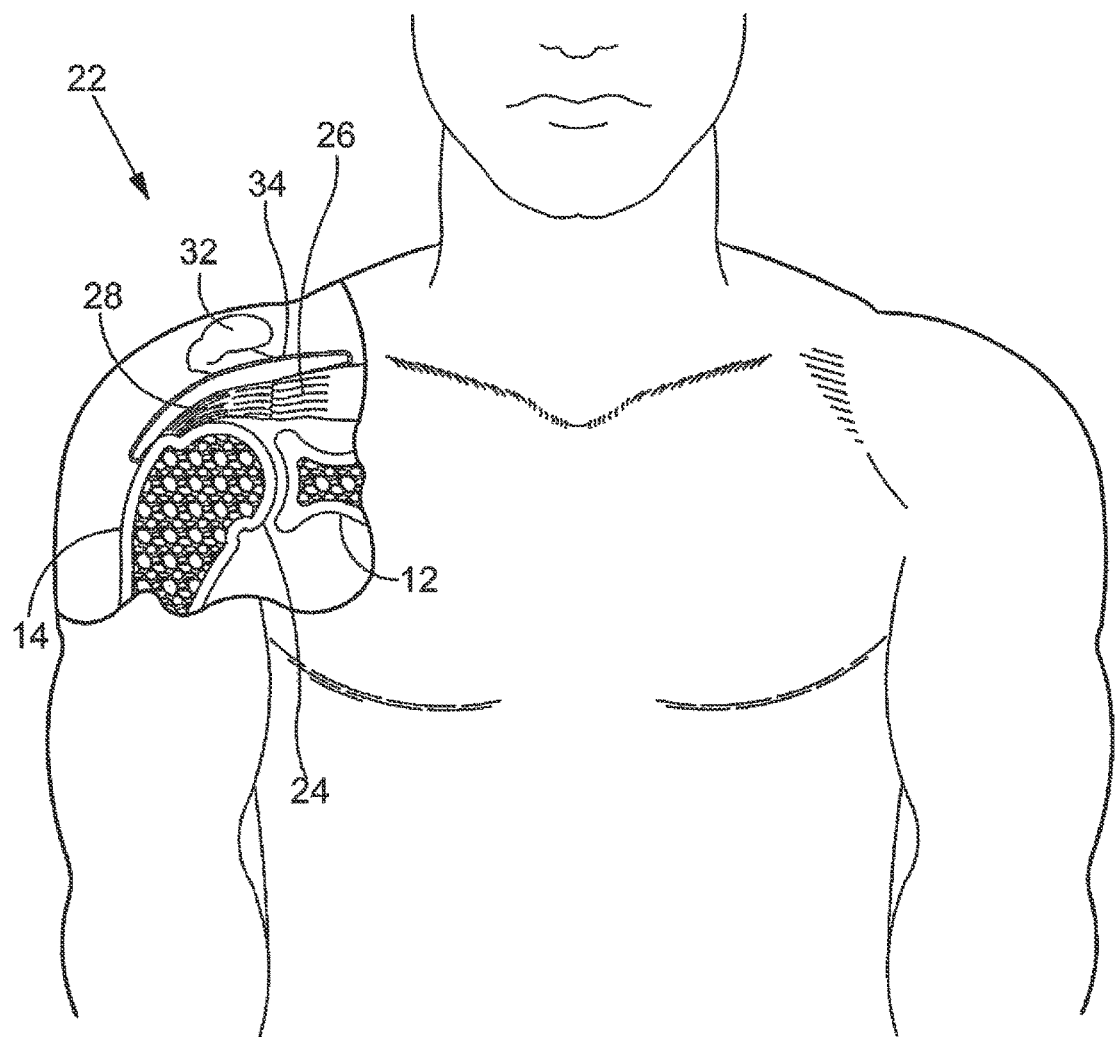
FIG. 3 is a stylized anterior view of a patient with a shoulder being shown in cross-section for purposes of illustration.

FIG. 3 is a stylized anterior view of a patient 20. For purposes of illustration, a shoulder 22 of patient 20 is shown in cross-section in FIG. 3. Shoulder 22 includes a humerus 14 and a scapula 12. In FIG. 3, a head 24 of humerus 14 can be seen mating with a glenoid fossa of scapula 12 at a glenohumeral joint. With reference to FIG. 3, it will be appreciated that the glenoid fossa comprises a shallow depression in scapula 12. The movement of humerus 14 relative to scapula 12 is controlled by a number of muscles including: the deltoid, the supraspinatus, the infraspinatus, the subscapularis, and the teres minor. For purposes of illustration, only the supraspinatus 26 is shown in FIG. 3.

With reference to FIG. 3, it will be appreciated that a distal tendon 28 of the supraspinatus 26 meets humerus 14 at an insertion point. Scapula 12 of shoulder 22 includes an acromium 32. In FIG. 3, a subacromial bursa 34 is shown extending between acromium 32 of scapula 12 and head 24 of humerus 14. In FIG. 3, subacromial bursa 34 is shown overlaying supraspinatus 26 as well as supraspinatus tendon 28 and a portion of humerus 14. Subacromial bursa 34 is one of the hundreds of bursae found the human body. Each bursa comprises a fluid filled sac. The presence of these bursae in the body reduces friction between bodily tissues. Injury and/or infection of the bursa can cause it to become inflamed. This condition is sometimes referred to as bursitis.

The exemplary methods and apparatus described herein may be used to affix tendon repair implants to various target tissues. For example, a tendon repair implant may be affixed to one or more tendons associated with an articulating joint, such as the glenohumeral joint. The tendons to be treated may be torn, partially torn, have internal micro-tears, be untorn, and/or be thinned due to age, injury or overuse. Applicants believe that the methods and apparatus of the present application and related devices may provide very beneficial therapeutic effect on a patient experiencing joint pain believed to be caused by partial thickness tears and/or internal microtears. By applying a tendon-repair implant early before a full tear or other injury develops, the implant may cause the tendon to thicken and/or at least partially repair itself, thereby avoiding more extensive joint damage, pain, and the need for more extensive joint repair surgery.

Figure 4:
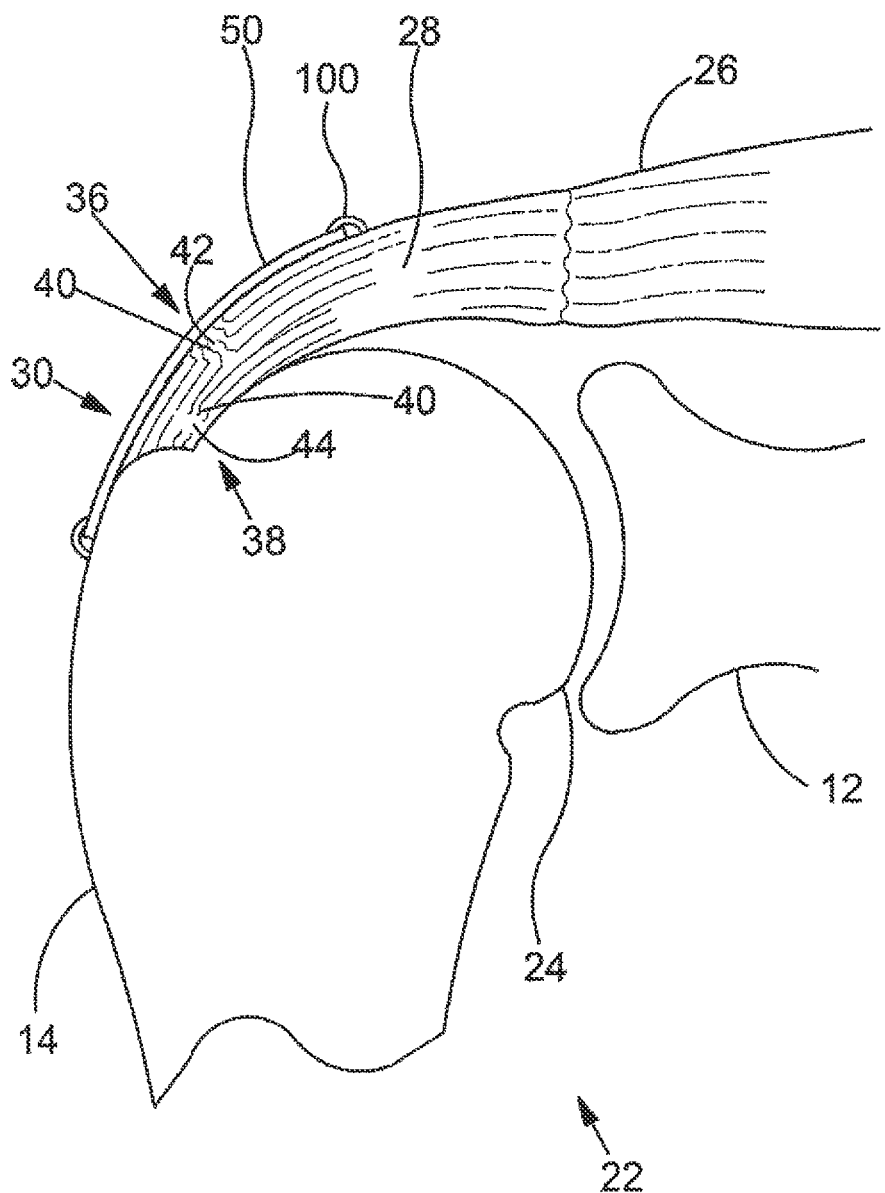
FIG. 4 is a stylized anterior view of a shoulder including a humerus and a scapula. The head of the humerus is shown mating with the glenoid fossa of the scapula at a glenohumeral joint.

FIG. 4 is a stylized anterior view of a shoulder 22 including a humerus 14 and a scapula 12. In FIG. 4, a head 24 of humerus 14 is shown mating with a glenoid fossa of scapula 12 at a glenohumeral joint. A supraspinatus 26 is also shown in FIG. 4. This muscle, along with others, control the movement of humerus 14 relative to scapula 12. A distal tendon 28 of supraspinatus 26 meets humerus 14 at an insertion point 30.

In the embodiment of FIG. 4, distal tendon 28 includes a first damaged portion 36. A number of loose tendon fibers 40 in first damaged portion 36 are visible in FIG. 4. First damaged portion 36 includes a first tear 42 extending partially through distal tendon 28. First tear 42 may therefore be referred to as a partial thickness tear. With reference to FIG. 4, it will be appreciated that first tear 42 begins on the side of distal tendon 28 facing the subacromial bursa (shown in the previous Figure) and ends midway through distal tendon 28. Accordingly, first tear 42 may be referred to as a bursal side tear.

With reference to FIG. 4, it will be appreciated that distal tendon 28 includes a second damaged portion 38 located near insertion point 30. In the embodiment of FIG. 4, second damaged portion 38 of distal tendon 28 has become frayed and a number of loose tendon fibers 40 are visible in FIG. 4. Second damaged portion 38 of distal tendon 28 includes second tear 44. With reference to FIG. 4, it will be appreciated that second tear 44 begins on the side of distal tendon 28 facing the center of the humeral head 24. Accordingly, second damaged portion 38 may be referred to as an articular side tear.

In the embodiment of FIG. 4, a sheet-like implant 50 has been placed over the bursal side of distal tendon 28. With reference to FIG. 4, it will be appreciated that sheet-like implant 50 extends over insertion point 30, first tear 42 and second tear 44. Some useful methods in accordance with this detailed description may include placing a tendon repair implant on the bursal side of a tendon regardless of whether the tears being treated are on the bursal side, articular side or within the tendon. In some cases the exact location and nature of the tears being treated may be unknown. A tendon repair implant may be applied to the bursal side of a tendon to treat shoulder pain that is most likely caused by one or more partial thickness tears in the tendon. In the embodiment of FIG. 4, sheet-like implant 50 is fixed to distal tendon 28 by a plurality of staples.

Figure 5A:
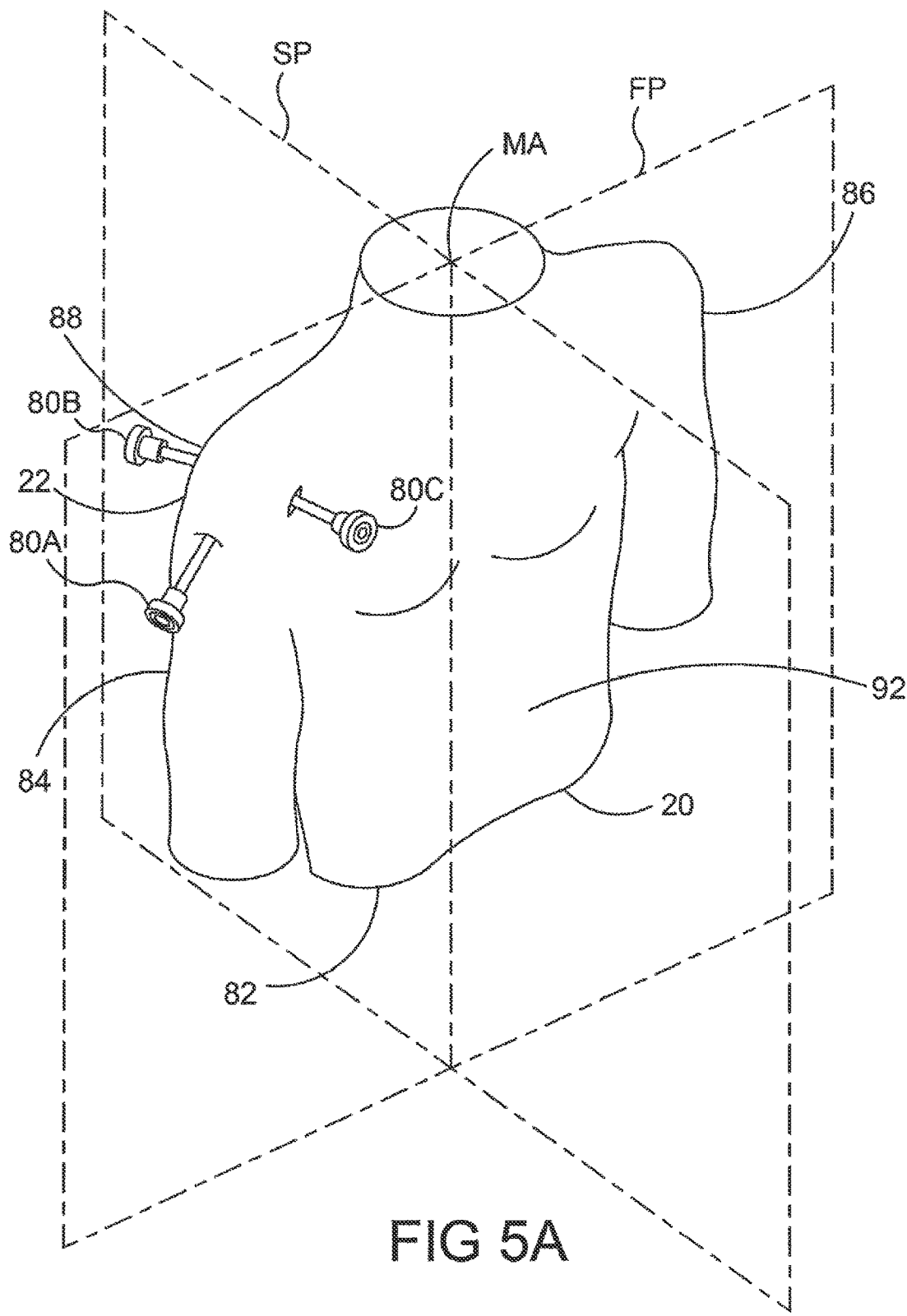
FIG. 5A is a stylized perspective view showing a portion of the body of a human patient.

FIG. 5A is a stylized perspective view showing a portion of the body 82 of a human patient 20. Body 82 includes a shoulder 22. In the exemplary embodiment of FIG. 5A, a plurality of cannulas are positioned to access a treatment site within shoulder 22. In some cases, shoulder 22 may be inflated by pumping a continuous flow of saline through shoulder 22 to create a cavity proximate the treatment site. The cannulas shown in FIG. 5A include a first cannula 80A, a second cannula 80B and a third cannula 80C.

In FIG. 5A, a sagital plane SP and a frontal plane FP are shown intersecting body 82. Sagital plane SP and frontal plane FP intersect one another at a medial axis MA of body 82. With reference to FIG. 5, it will be appreciated that sagital plane SP bisects body 82 into a right side 84 and a left side 86. Also with reference to FIG. 5, it will be appreciated that frontal plane FP divides body 82 into an anterior portion 92 and a posterior portion 88. In the embodiment of FIG. 5, sagital plane SP and a frontal plane FP are generally perpendicular to one another.

In the exemplary embodiment of FIG. 5, first cannula 80A is accessing a treatment site within shoulder 22 using a lateral approach in which first cannula 80A pierces the outer surface of right side 84 of body 82. The term lateral approach could also be used to describe situations in which an instrument pierces the outer surface of left side 86 of body 82. In the exemplary embodiment of FIG. 5, second cannula 80B is accessing a treatment site within shoulder 22 using a posterior approach in which second cannula 80B pierces the outer surface of posterior portion 88 of body 82. In the exemplary embodiment of FIG. 5, third cannula 80C is accessing a treatment site within shoulder 22 using an anterior approach in which third cannula 80C pierces the outer surface of anterior portion 92 of body 82.

Figure 5B:
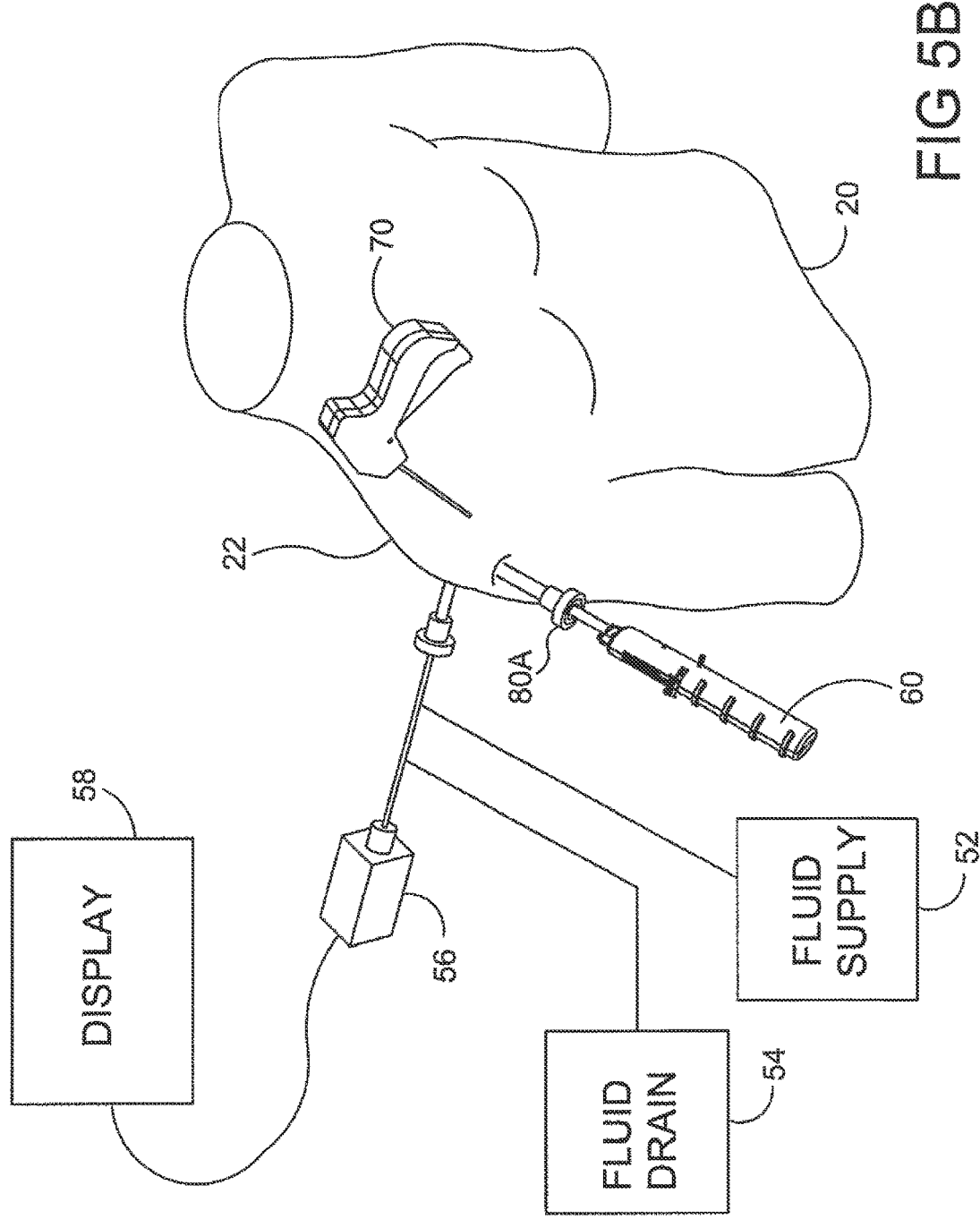
FIG. 5B is a stylized perspective view illustrating an exemplary procedure for treating a shoulder of a patient.

FIG. 5B is a stylized perspective view illustrating an exemplary procedure for treating a shoulder 22 of a patient 20. The procedure illustrated in FIG. 5B may include, for example, fixing tendon repair implants to one or more tendons of shoulder 22. The tendons treated may be torn, partially torn, have internal micro-tears, be untorn, and/or be thinned due to age, injury or overuse.

Shoulder 22 of FIG. 5B has been inflated to create a cavity therein. In the exemplary embodiment of FIG. 5B, a fluid supply 52 is pumping a continuous flow of saline into the cavity. This flow of saline exits the cavity via a fluid drain 54. A camera 56 provides images from inside the cavity. The images provided by camera 56 may be viewed on a display 58.

Camera 56 may be used to visually inspect the tendons of shoulder 22 for damage. A tendon repair implant in accordance with this disclosure may be affixed to a bursal surface of the tendon regardless of whether there are visible signs of tendon damage. Applicants believe that the methods and apparatus of the present application and related devices may provide very beneficial therapeutic effect on a patient experiencing joint pain believed to be caused by internal microtears, but having no clear signs of tendon tears. By applying a tendon repair implant early before a full tear or other injury develops, the implant may cause the tendon to thicken and/or at least partially repair itself, thereby avoiding more extensive joint damage, pain, and the need for more extensive joint repair surgery.

An implant delivery system 60 can be seen extending from shoulder 22 in FIG. 5B. With reference to FIG. 5B, it will be appreciated that implant delivery system 60 is extending through a first cannula 80A. In the exemplary embodiment of FIG. 5, first cannula 80A is accessing a treatment site within shoulder 22 using a lateral approach in which first cannula 80A pierces the outer surface of a right side of the patient's body. In some cases a physician may choose not to use a cannula in conjunction with implant delivery system 60. When that is the case, the implant delivery system may be advanced through tissue. Implant delivery system 60 comprises a sheath that is fixed to a handle. The sheath defines a lumen and a distal opening fluidly communicating with the lumen. In the embodiment of FIG. 5B, the distal opening of the sheath has been placed in fluid communication with the cavity created in shoulder 22.

A tendon repair implant is at least partially disposed in the lumen defined by the sheath of implant delivery system 60. Implant delivery system 60 can be used to place the tendon repair implant inside shoulder 22. In some embodiments, the tendon repair implant is folded into a compact configuration when inside the lumen of the sheath. When this is the case, implant delivery system 60 may be used to unfold the tendon repair implant into an expanded shape. Additionally, implant delivery system 60 can be used to hold the tendon repair implant against the tendon.

The tendon repair implant may be affixed to the tendon while it is held against the tendon by implant delivery system 60. Various attachment elements may be used to fix the tendon-repair implant to the tendon. Examples of attachment elements that may be suitable in some applications include sutures, tissue anchors, bone anchors, and staples. In the exemplary embodiment of FIG. 5B, the shaft of a fixation tool 70 is shown extending into shoulder 22. In one exemplary embodiment, fixation tool 70 is capable of fixing the tendon repair implant to the tendon with one or more staples while the tendon repair implant is held against the tendon by implant delivery system 60.

Figure 6:
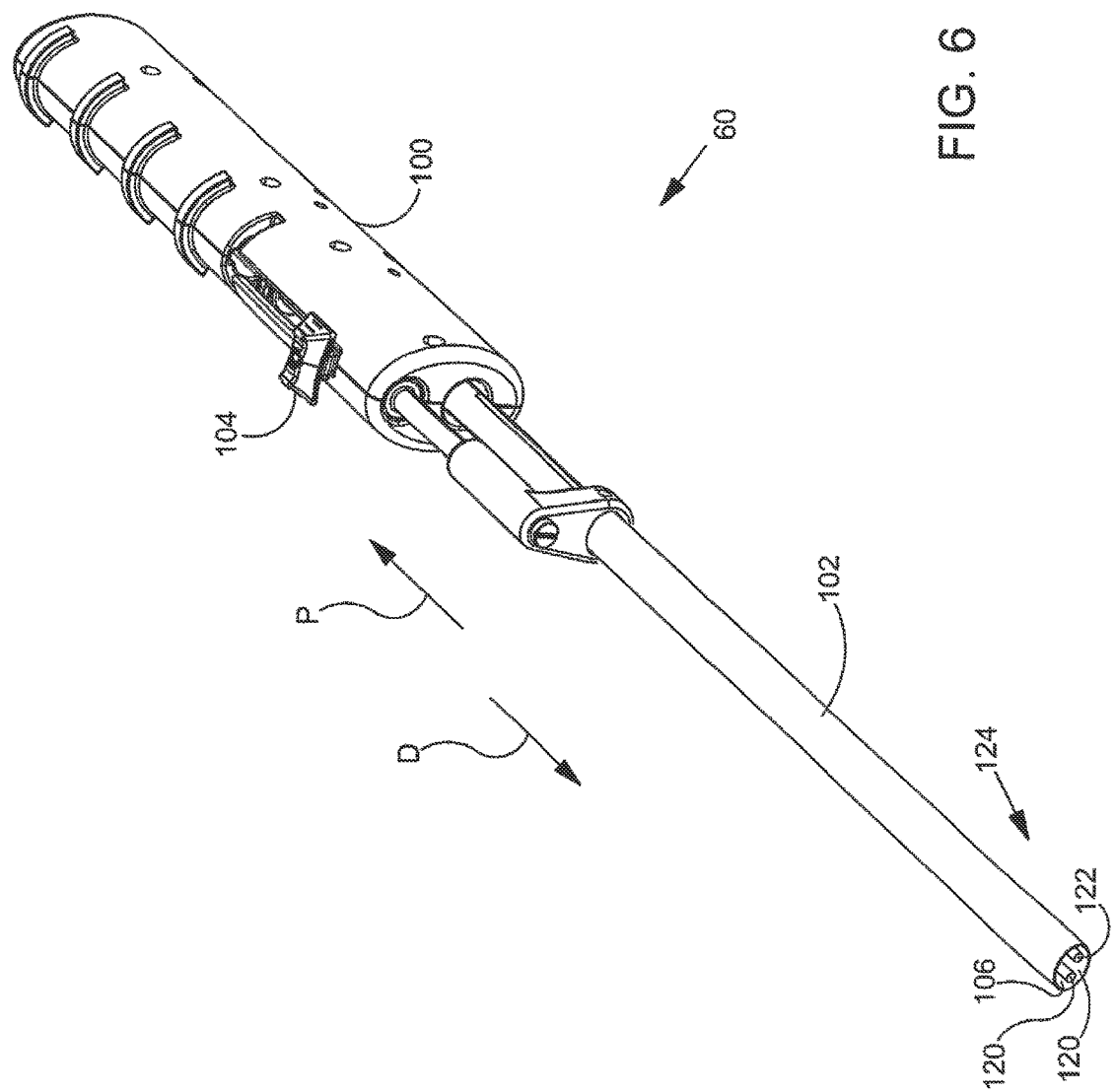
FIG. 6 is an enlarged perspective view illustrating an embodiment of the implant delivery system.

FIG. 6 is an enlarged perspective view further illustrating implant delivery system 60 shown in the previous figure. Implant delivery system 60 includes a handle 100 and a sheath 102. Sheath 102 of implant delivery system 60 is coupled to a button 104 that may be used to move sheath 102 in a distal direction D and/or a proximal direction P. Distal direction D and proximal direction P are illustrated with arrows in FIG. 6. In the exemplary embodiment of FIG. 6, relative motion between button 104 and handle 100 will cause similar relative motion between sheath 102 and handle 100. In the exemplary embodiment of FIG. 6, sheath 102 will be moved distally (relative to handle 100) when button 104 is moved distally (relative to handle 100). Additionally, sheath 102 will be moved proximally (relative to handle 100) when button 104 is moved proximally (relative to handle 100). It will be appreciated that various other operative mechanisms may be used in addition to button 104 in order to move sheath 102 distally and/or proximally.

Sheath 102 of implant delivery system 60 defines a lumen 106 and a distal opening 108 fluidly communicating with lumen 106. In FIG. 6, a first arm 120 and a second arm 122 can be seen residing in lumen 106. First arm 120 and second arm 122 are both part of an implant spreader assembly 124. Implant spreader assembly 124 may be used to carry a sheet-like implant to a location within the human body. Implant spreader assembly 124 may also be used to unfold the sheet-like implant so that the sheet-like implant covers a treatment site within the body.

FIG. 7 is an additional perspective view further illustrating implant delivery system 60 shown in the previous figure. In the exemplary embodiment of FIG. 7, sheath 102 has been retracted so that sheath 102 is resting in a position more proximal than the position shown in the previous figure. With reference to FIG. 7, it will be appreciated that sheath 102 has been retracted far enough so that first arm 120 and second arm 122 of implant spreader assembly 124 are both uncovered from sheath 102. First arm 120 includes a proximal end 126A and a distal end 128A. Second arm 122 has a proximal end 126B and a distal end 128B. The proximal end of each arm is pivotably connected to a delivery shaft 130 of implant delivery system 60. In FIG. 7, delivery shaft 130 is shown extending along a longitudinal axis 132.

In the exemplary embodiment of FIG. 7, first arm 120 and second arm 122 are disposed in a closed position. First arm 120 and second arm 122 are capable of moving between the closed position shown in FIG. 7 and an open position. With reference to FIG. 7, it will be appreciated that first arm 120 and second arm 122 extend in a longitudinal direction that is generally parallel to longitudinal axis 132 when the arms are in the closed position. When pivoting to the open position the arms rotate so that distal end 128A of first arm 120 and distal end 128B of second arm 122 move away from each other in generally transverse directions. A sheet-like implant may be coupled to implant spreader assembly 124 in such a way that the implant is folded when the arms of implant spreader assembly 124 are in the closed position and unfolded when the arms of implant spreader assembly 124 are in the open position.

FIG. 8 is an additional perspective view further illustrating implant delivery system 60 shown in the previous figure. In the exemplary embodiment of FIG. 8, first arm 120 and second arm 122 of implant spreader assembly 124 have been moved away from the closed position shown in the previous figure. With reference to the previous figure, it will be appreciated that the arms have been rotated so that distal end 128A of first arm 120 and distal end 128B of second arm 122 have moved away from each other in generally transverse directions. Accordingly, it will be appreciated that proximal end 126A of first arm 120 and proximal end 126B of second arm 122 are both pivotably coupled to delivery shaft 130 in the embodiment of FIG. 8. In FIG. 8, the distal ends of the arms lie in the same plane as the sheath in both the open and closed positions, however, in other embodiments disclosed herein, the arms may move in different planes relative to each other so that the implant will take a curved shape in the open position to better conform to the treatment site as laterally delivered.

The position of first arm 120 and second arm 122 in the embodiment of FIG. 8 may be referred to as an open position. In the embodiment of FIG. 8, first arm 120 and second arm 122 are capable of moving between the open position shown in FIG. 8 and the closed position shown in the previous figure. The arms may be moved back to the closed position by rotating the arms so that distal end 128A of first arm 120 and distal end 128B of second arm 122 move toward each other in generally transverse directions. In some useful embodiments, a sheet-like implant is coupled to first arm 120 and second arm 122 of implant spreader assembly 124. When this is the case, implant spreader assembly 124 may also be used to unfold the sheet-like implant so that the sheet-like implant covers a treatment site within the body. In alternative embodiments, the first arm 120 and second arm 122 can be actuated by the user or can be self-actuating when the sheath 102 is retracted. Further, the embodiment of FIG. 8 depicts both the first arm 120 and the second arm 122 moveable. In alternative embodiments, one arm may be stationary while the other rotates to spread the implant.

FIG. 9A through FIG. 9C are a series of stylized perspective views illustrating at least part of an exemplary method in accordance with the present detailed description. This method may be used, for example, to deliver a sheet-like implant 50 into the human body while implant 50 is arranged to fit within a relatively compact volume defined by a sheath 102. This exemplary process may also be used to expand implant 50 to cover a treatment site within the body. FIG. 9A through FIG. 9C may be referred to collectively as FIG. 9. A proximal direction is illustrated with an arrow P in FIG. 9.

FIG. 9A is a perspective view showing a distal portion of an implant delivery system 60. Implant delivery system 60 includes a sheath 102 defining a lumen 106 and a distal opening 108 fluidly communicating with lumen 106. In FIG. 9A, a sheet-like implant 50 can be seen residing in lumen 106. A distal end 128A of a first arm 120 and a distal end 128B of a second arm 122 are also visible in FIG. 9A. First arm 120 and second arm 122 are both part of an implant spreader assembly 124. In the embodiment of FIG. 9A, a central portion 134 of implant 50 is folded between first arm 120 and second arm 122 of implant spreader assembly 124. In the exemplary embodiment of FIG. 9A, implant 50 is coupled to first arm 120 and second arm 122 in such a way that central portion 134 of implant 50 is folded between the arms when the arms are in the closed position shown in FIG. 9A.

In the exemplary embodiment of FIG. 9A, implant 50 is arranged to fit within lumen 106 defined by sheath 102. In the embodiment of FIG. 9A, sheath 102 is slidable in a proximal direction P. Accordingly, sheath 102 can be retracted proximally from around implant 50 and the implant spreader assembly 124. An exemplary method in accordance with the present detailed description may include the step of retracting sheath 102 proximally from around implant 50 and implant spreader assembly 124 and unfolding implant 50 using implant spreader assembly 124. In FIG. 9A, a central portion 134 of implant 50 can be seen folded between first arm 120 and second arm 122. Implant 50 may be unfolded by spreading the arms of implant spreader assembly 124 apart while implant 50 is outside of sheath 102. In this way, implant 50 may be expanded so that the sheet-like implant covers a treatment site within the body.

In the exemplary embodiment of FIG. 9A, implant 50 is arranged to fit within the relatively compact volume defined by sheath 102. With reference to FIG. 9, it will be appreciated that implant 50 is arranged within sheath 102 such that the shape of a distal edge 136 of implant 50 substantially corresponds to the shape of the upper case omega in the Greek alphabet. In the embodiment of FIG. 9, implant 50 is arranged within sheath 102 such that the shape of a proximal edge 138 of implant 50 substantially corresponds to the shape of the lower case omega in the Greek alphabet.

FIG. 9B is an additional perspective view showing the distal portion of implant delivery system 60 shown in FIG. 9A. By comparing FIG. 9B and FIG. 9A, it will be appreciated that sheath 102 has been withdrawn in a proximal direction P. In the exemplary embodiment of FIG. 9B, sheath 102 has been refracted so that a portion of implant 50 is uncovered and sheath 102 is resting in a position more proximal than the position shown in the FIG. 9A.

In the exemplary embodiment illustrated in FIG. 9B, the portion of implant 50 outside of sheath 102 has assumed a somewhat expanded shape. Implant 50 may comprise various materials without deviating from the spirit and scope of the present invention. In some cases, the material of implant 50 may be sufficiently resilient that implant 50 assumes an expanded shape when the implant is freed from sheath 102. The extent to which implant 50 assumes an expanded shape is likely to vary depending upon the resilience of the implant material to reform to its original shape prior to compaction within lumen 106 as defined by sheath 102.

FIG. 9C is an additional perspective view showing the distal portion of implant delivery system 60 shown in FIG. 9B. In the embodiment of FIG. 9C, sheath 102 has been retracted in proximal direction P such that implant 50 is completely outside of lumen 106 defined by sheath 102. With reference to FIG. 9C, it will be appreciated that implant 50 is carried by first arm 120 and second arm 122 of an implant spreader assembly 124. In FIG. 9, the arms of implant spreader assembly 124 are shown in a closed position with a central portion 134 of implant 50 folded between first arm 120 and second arm 122. Also in FIG. 9, the central portion 134 of implant 50 is shown defining a trough 140. In the embodiment of FIG. 9, trough 140 has a depth that varies between a proximal edge 138 of implant 50 and a distal edge 136 of implant 50.

In the embodiment of FIG. 9, first arm 120 and second arm 122 are capable of moving between the closed position shown in FIG. 9 and an open position. With reference to FIG. 9 it will be appreciated that first arm 120 and second arm 122 extend in a longitudinal direction that is generally parallel to a longitudinal axis 132 when the arms are in the closed position. When pivoting to the open position the arms rotate so that distal end 128A of first arm 120 and distal end 128B of second arm 122 move away from each other. Implant 50 is arranged on implant spreader assembly 124 so that implant 50 is folded when the arms of implant spreader assembly 124 are in the closed position and unfolded when the arms of implant spreader assembly 124 are in the open position.

FIG. 10A and FIG. 10B are a pair of stylized perspective views illustrating the open and closed positions that may be assumed by first arm 120 and second arm 122 of implant spreader assembly 124. FIG. 10A and FIG. 10B may be referred to collectively as FIG. 10. A proximal direction is illustrated with an arrow P in FIG. 10. A distal direction is illustrated with another arrow D in FIG. 10.

FIG. 10A is a perspective view showing a first arm 120 and a second arm 122 of implant spreader assembly 124. With reference to FIG. 10A it will be appreciated that first arm 120 and second arm 122 are assuming the closed position in which the arms extend in a longitudinal direction that is generally parallel to a longitudinal axis 132. When pivoting to the open position the arms rotate so that distal end 128A of first arm 120 and distal end 128B of second arm 122 move away from each other.

In FIG. 10A, a plurality of suture loops 146 are shown coupling implant 50 to first arm 120 and second arm 122. In the embodiment of FIG. 10A, implant 50 is arranged relative to implant spreader assembly 124 such that implant 50 is folded when the arms of implant spreader assembly 124 are in the closed position and unfolded when the arms of implant spreader assembly 124 are in the open position. In FIG. 10A, the arms of implant spreader assembly 124 shown in a closed position with a central portion 134 of implant 50 folded between first arm 120 and second arm 122. Also in FIG. 10A, the central portion 134 of implant 50 is shown defining a trough 140. In the embodiment of FIG. 10A, trough 140 has a depth that varies between a proximal edge 138 of implant 50 and a distal edge 136 of implant 50.

FIG. 10B is an additional perspective view illustrating implant 50 and the arms of implant spreader assembly 124 shown in the previous figure. In the exemplary embodiment of FIG. 10B, first arm 120 and second arm 122 of implant spreader assembly 124 have been rotated so that they are assuming an open position. With reference to the previous figure, it will be appreciated that the arms have been rotated so that distal end 128A of first arm 120 and distal end 128B of second arm 122 have moved away from each other in generally transverse directions.

In FIG. 10B, central portion 134 of implant 50 can be seen extending between first arm 120 and second arm 122. In some useful embodiments, implant 50 can be pulled tautly between first arm 120 and second arm 122. In the embodiment of FIG. 10B, implant 50 overlaying a target tissue 142 having a generally curved outer surface 144. Implant 50 is pulled tautly over target tissue 142 so that implant 50 is conforming to the generally curved outer surface 144 of target tissue 142. In one embodiment, the first arm 120 and second arm 122 move laterally such that the distal ends lie in a plane different from the sheath. This movement aids in allowing the implant to take on a curved shape as illustrated and better conform to the anatomy of the shoulder.

Implant 50 may be fixed to the target tissue 142 while it is held against the target tissue 142 by first arm 120 and second arm 122 of implant spreader assembly 124. Various attachment elements may be used to fix implant 50 to target tissue 142. Examples of attachment elements that may be suitable in some applications include sutures, tissue anchors, bone anchors, and staples. Implant spreader assembly 124 can be separated from implant 50 by moving first arm 120A and second arm 122B a proximal direction P so that the arms are withdrawn from suture loops 146. The arms may be withdrawn from suture loops 146 with or without movement of distal end 128A and distal end 128B closer together.

Figure 11:
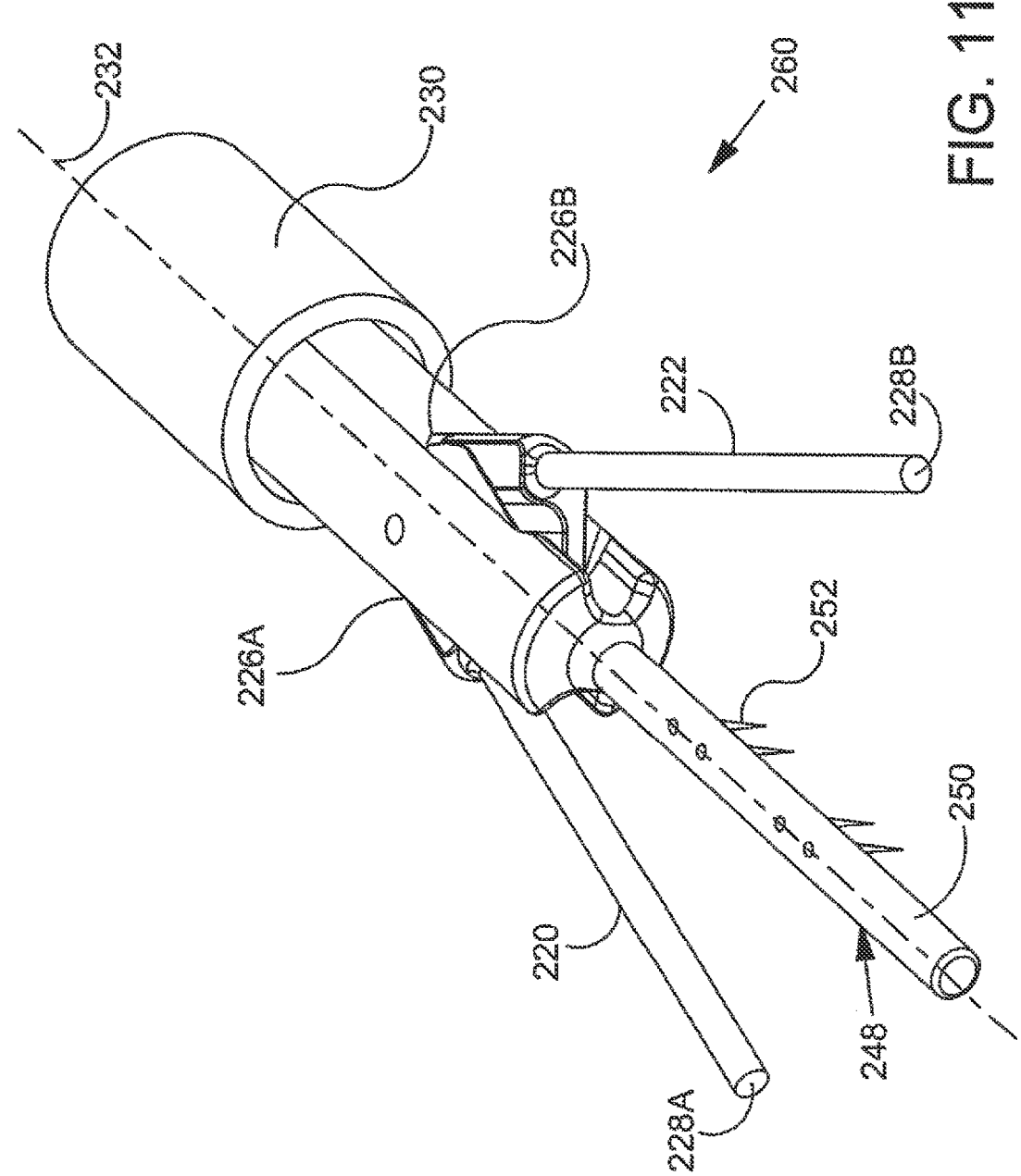
FIG. 11 is a perspective view showing a distal portion of an implant delivery system useful for delivering a sheet-like implant to a target location within a human body.

FIG. 11 is a perspective view showing a distal portion of an implant delivery system 260 useful for delivering a sheet-like implant to a target location within a human body. Implant delivery system 260 comprises a delivery shaft 230 extending along a longitudinal axis 232. Implant delivery system 260 also includes an implant retainer assembly 248 and an implant spreader assembly 224 that are both located near a distal end of delivery shaft 230. In the exemplary embodiment of FIG. 11, implant retainer assembly 248 comprises a center post 250 carrying a plurality of spikes 252. Spikes 252 are configured to releasably couple a sheet-like implant to center post 250 for positioning the sheet-like implant at a treatment site.

Implant spreader assembly 224 of implant delivery system 260 comprises a first arm 220 and a second arm 222. First arm 220 has a proximal end 226A and a distal end 228A. Second arm 222 has a distal end 228B and a proximal end 226B. The proximal end of each arm is pivotably connected to delivery shaft 230. First arm 220 and second arm 222 are moveable between a closed position and an open position. In FIG. 11, first arm 220 and second arm 222 are shown in the open position. When the arms are disposed in the closed position, the arms extend in a longitudinal direction that is generally parallel to longitudinal axis 232 of delivery shaft 230. When the arms pivot to the open position the distal end of each arm moves in a generally transverse direction. First arm 220 and second arm 222 may be used to spread an implant positioned on implant retainer assembly 248 as the arms pivot to the open position.

Figure 12:
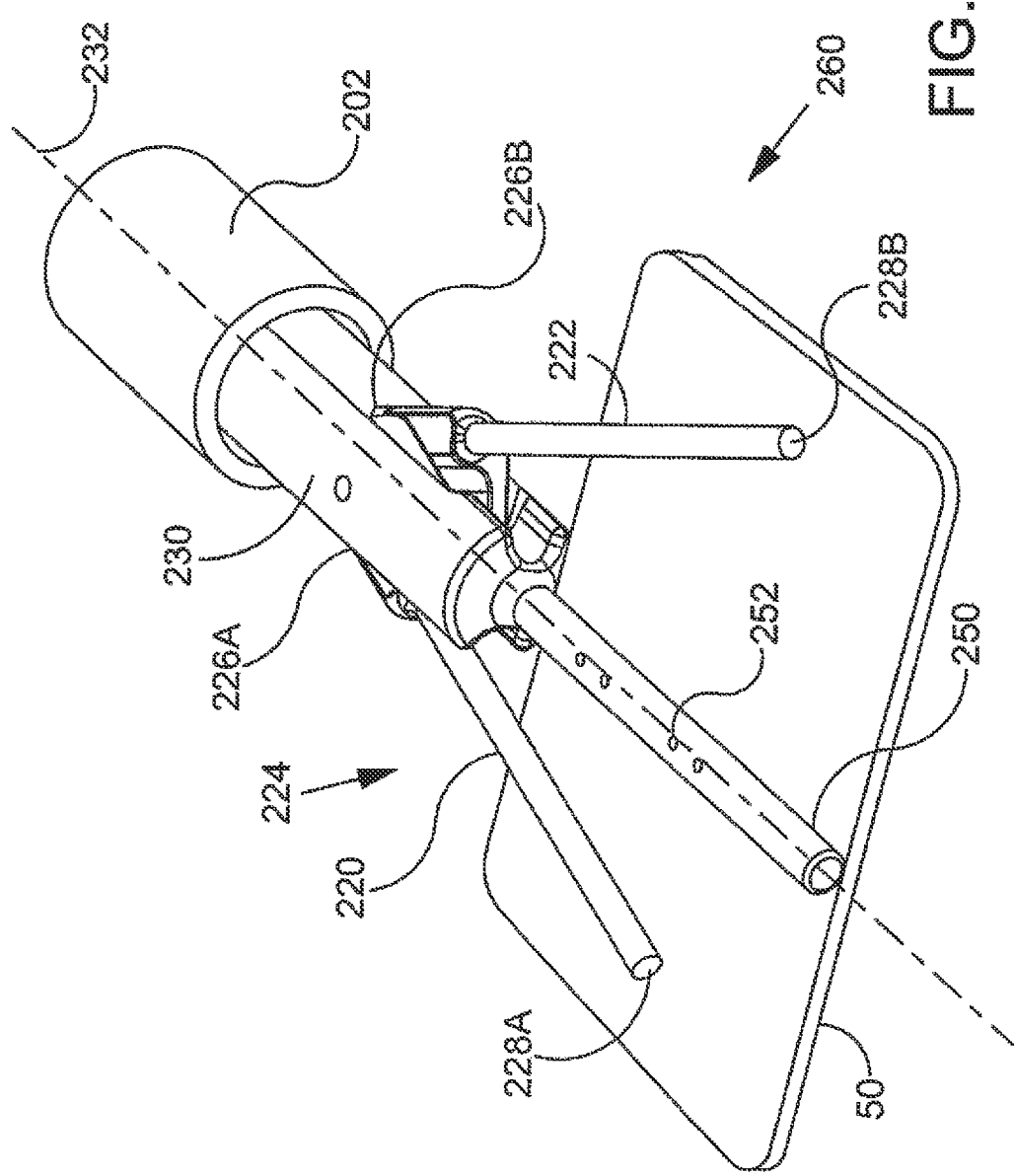
FIG. 12 is a perspective view showing an additional exemplary embodiment of implant delivery system shown in the previous figure.

FIG. 12 is a perspective view showing an additional exemplary embodiment of implant delivery system 260 shown in the previous figure. In the exemplary embodiment of FIG. 12, a sheet-like implant 50 is releasably coupled to center post 250 by a plurality of spikes 252. Each spike 252 extends through center post 250 and into implant 50. Spikes 252 are configured to releasably couple implant 50 to center post 250 for positioning sheet-like implant 50 at a treatment site.

In the exemplary embodiment of FIG. 12, implant delivery system 260 includes a sheath 202 disposed about delivery shaft 230. Sheath 202 is slidable in a direction generally parallel to longitudinal axis 232 of delivery shaft 230 such that sheath 202 can selectively cover and uncover implant 50. Implant 50 may be rolled into a relatively compact shape so that implant 50 fits within the volume defined by sheath 202. Sheath 202 can be moved distally so that sheath 202 covers implant 50 while the implant is rolled into a relatively compact shape.

Methods in accordance with this detailed description may include uncovering the implant (by withdrawing the sheath) and unrolling the implant. Implant spreader assembly 224 may be used to unroll implant 50. Implant spreader assembly 224 has a first arm 220 and a second arm 222. First arm 220 has a proximal end 226A and a distal end 228A. Second arm 222 has a distal end 228B and a proximal end 226B. The proximal end of each arm is pivotably connected to delivery shaft 230. In FIG. 12, first arm 220 and second arm 222 are shown in an open position. First arm 220 and second arm 222 may be used to unroll implant 50 as the arms move from a closed position to the open position shown in FIG. 12.

Figure 13:
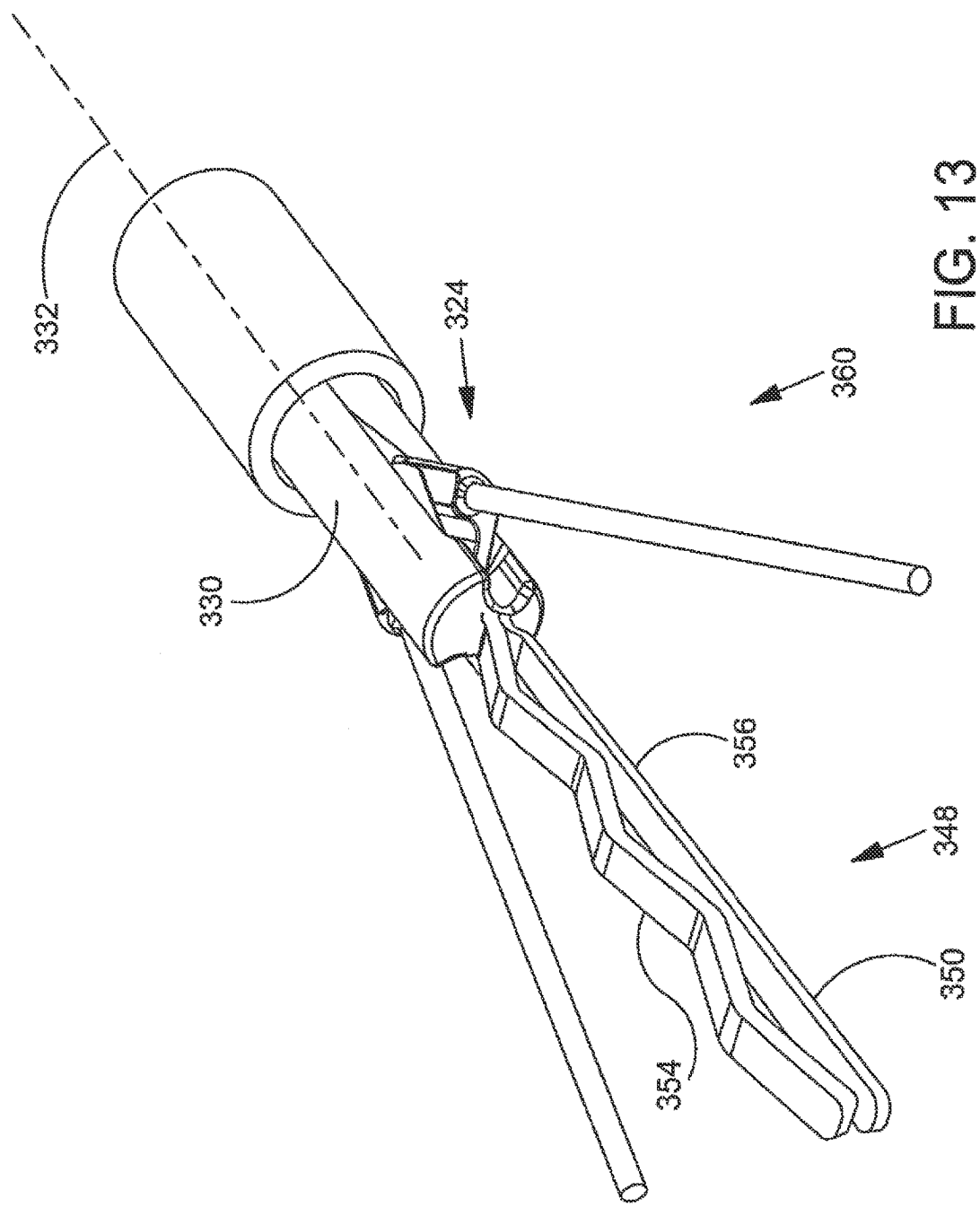
FIG. 13 is a perspective view illustrating an additional embodiment of an implant delivery system in accordance with the detailed description.

FIG. 13 is a perspective view illustrating an additional embodiment of the distal portion of implant delivery system 360 in accordance with the present detailed description. Implant delivery system 360 of FIG. 13 comprises a delivery shaft 330 extending along a longitudinal axis 332. An implant retainer assembly 348 and an implant spreader assembly 324 are located near a distal end of delivery shaft 330. In the exemplary embodiment of FIG. 13, implant retainer assembly 348 comprises a center post 350 including an upper finger 354 and a lower finger 356. It will be appreciated that the adjectives upper and lower are used herein as a convenient method for differentiating between the two fingers shown in FIG. 13. It will also be understood that implant delivery system 360 may assume various orientations without deviating from the spirit and scope of this detailed description. Accordingly, the adjectives upper and lower should not be interpreted to limit the scope of the invention recited in the attached claims.

In the embodiment of FIG. 13, upper finger 354 and lower finger 356 of center post 350 define a slot that is dimensioned to receive a sheet-like implant A sheet-like implant may be positioned between upper finger 354 and lower finger 356 so that the implant is releasably coupled to implant retainer assembly 348 for positioning the sheet-like implant at a treatment site. In the embodiment of FIG. 13, lower finger 356 has a substantially flat shape such that the sheet-like implant will lay substantially flat over a treatment site while lower finger 356 is disposed between the sheet-like implant and the treatment site. Upper finger 354 has an undulating shape including a plurality of bends such that upper finger 354 will contact the sheet-like implant in some areas and separate from the sheet-like implant in other areas.

Figure 14:
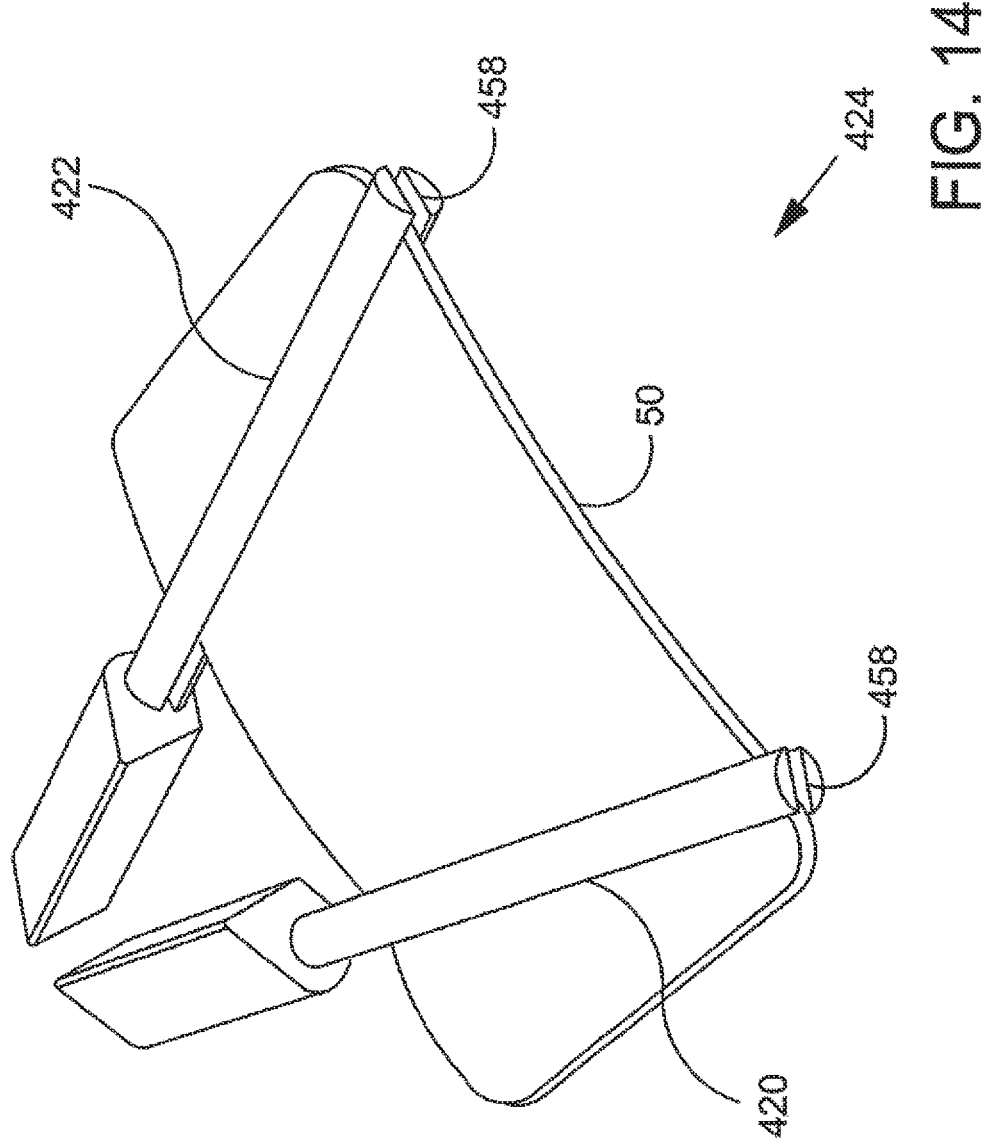
FIG. 14 is a perspective view showing a first arm and a second arm of an implant spreader assembly in accordance with another exemplary embodiment.

FIG. 14 is a perspective view showing a first arm 420 and a second arm 422 of an implant spreader assembly 424 in accordance with another exemplary embodiment. With reference to FIG. 14, it will be appreciated that first arm 420 and second arm 422 are carrying an implant 50. In the exemplary embodiment of FIG. 14, first arm 420 and second arm 422 of implant spreader assembly 424 are assuming an open position so that implant 50 is expanded. First arm 420 and second arm 422 each define a slot 458 in the embodiment of FIG. 14. In FIG. 14, portions of implant 50 are disposed in each slot 458. Each slot 458 is configured to releasably couple implant 50 to an arm for positioning the sheet-like implant at a treatment site.

Figure 15:
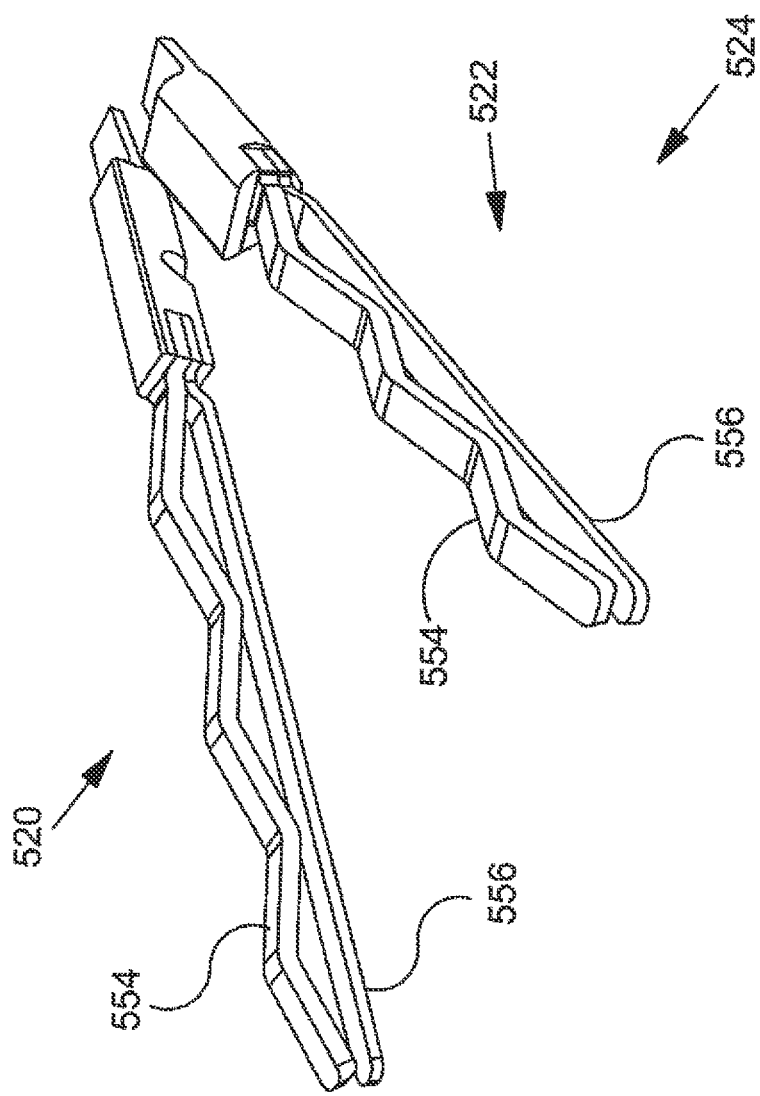
FIG. 15 is a perspective view showing a first arm and a second arm of an implant spreader assembly in accordance with an additional exemplary embodiment.

FIG. 15 is a perspective view showing a first arm 520 and a second arm 522 of an implant spreader assembly 524 in accordance with an additional exemplary embodiment. First arm 520 and second arm 522 are configured to releasably hold sheet-like implant for positioning the implant at a treatment site. In the exemplary embodiment of FIG. 15, each arm includes an upper finger 554 and a lower finger 556. It will be appreciated that the adjectives upper and lower are used herein as a convenient method for differentiating between the two fingers shown in FIG. 15. It will also be understood that the arms shown in FIG. 15 may assume various orientations without deviating from the spirit and scope of this detailed description. Accordingly, the adjectives upper and lower should not be interpreted to limit the scope of the invention recited in the attached claims. A sheet-like implant may be positioned between the upper finger 554 and the lower finger 556 of each arm so that the implant is releasably coupled to an implant delivery system for positioning the sheet-like implant at a treatment site. In the embodiment of FIG. 15, each lower finger 556 has a substantially flat shape such that the sheet-like implant will lay substantially flat over a treatment site while the lower fingers are disposed between the sheet-like implant and the treatment site. Each upper finger 554 has an undulating shape including a plurality of bends such that the upper finger will contact the sheet-like implant in some areas and separate from the sheet-like implant in other areas.

Figure 16:
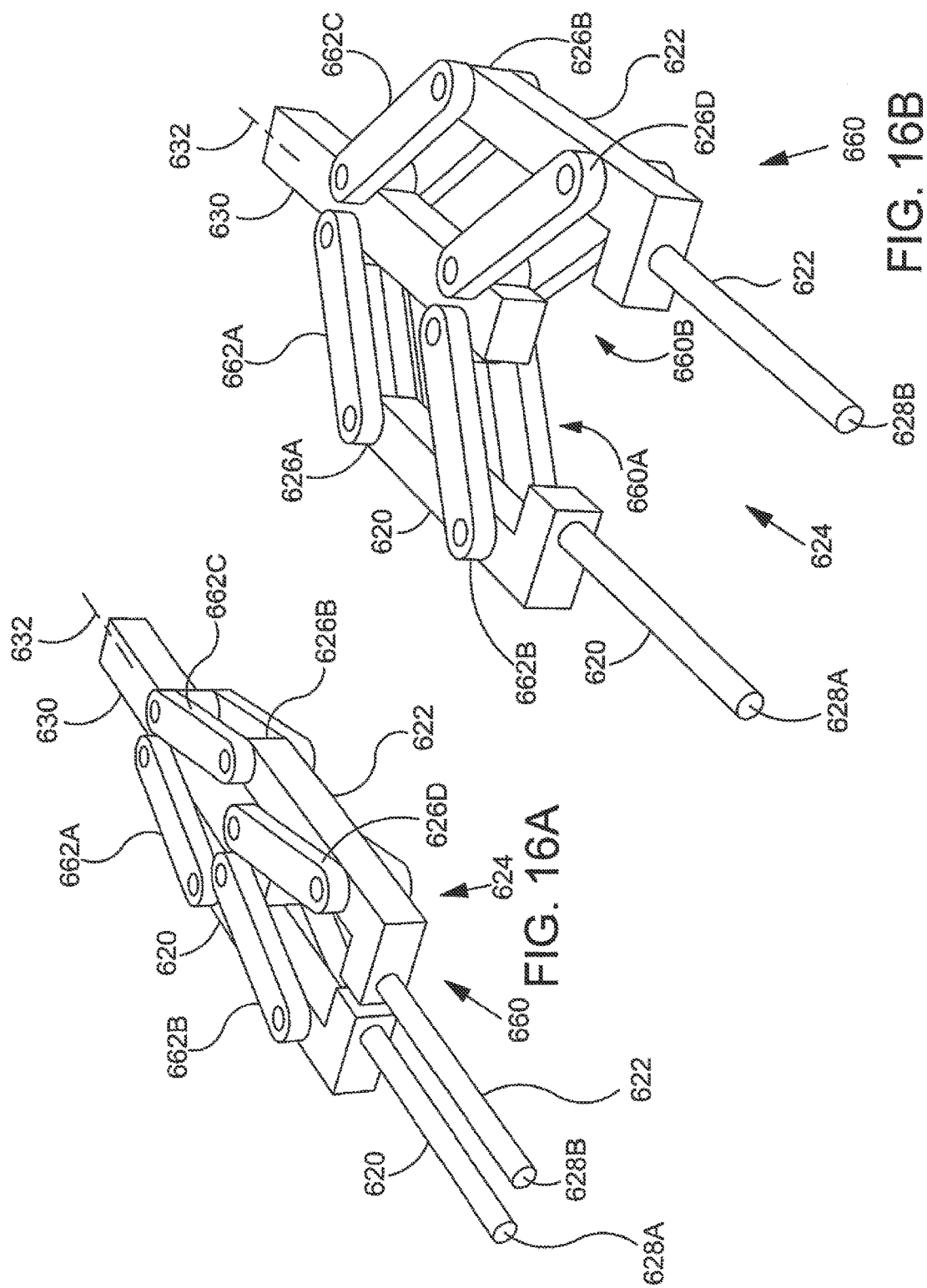
FIG. 16A and FIG. 16B are a pair of stylized perspective views illustrating another exemplary implant delivery system in accordance with the detailed description.

FIG. 16A and FIG. 16B are a pair of stylized perspective views illustrating another exemplary implant delivery system 660 in accordance with this detailed description. FIG. 16A and FIG. 16B will be collectively referred to as FIG. 16. Implant delivery system 660 of FIG. 16 comprises a first arm 620 and second arm 622. In the embodiment of FIG. 16, first arm 620 and second arm 622 are capable of moving between a closed position (illustrated in FIG. 16A) and an open position (illustrated in FIG. 16B).

First arm 620 and second arm 622 are both part of an implant spreader assembly 624. In the embodiment of FIG. 16, implant spreader assembly 624 includes a first four bar linkage 660A and a second four bar linkage 660B. First four bar linkage 660A of implant spreader assembly 624 comprises first arm 620, a delivery shaft 630, a first link 662A and a second link 662B. First arm 620 includes a proximal end 626A and a distal end 628A. In FIG. 16, first link 662A can be seen extending between proximal end 626A of first arm 620 and delivery shaft 630. First link 662A is pivotably coupled to both delivery shaft 630 and first arm 620. Second link 662B is also pivotably coupled to both delivery shaft 630 and first arm 620 in the embodiment of FIG. 16.

Second arm 622 of implant spreader assembly 624 has a proximal end 626B and a distal end 628B. Proximal end 626B of second arm 622 is pivotably coupled to a first end of a third link 662C. A second end of third link 662C is pivotably coupled to delivery shaft 630. In FIG. 16, a fourth link 662D can be seen extending between second arm 622 and delivery shaft 630 A first end of fourth link 662D is pivotably coupled to second arm 622 at a location between proximal end 626B and distal end 628B thereof. A second end of fourth link 662D is pivotably coupled to delivery shaft 630. Second arm 622, delivery shaft 630, a third link 662C and a fourth link 662D form a second four bar linkage 660B of implant spreader assembly 624.

First arm 620 and second arm 622 are capable of moving from the closed position shown in FIG. 16A to the open position shown in FIG. 16B. In some useful embodiments, a sheet-like implant is coupled to first arm 620 and second arm 622 of implant spreader assembly 624. When this is the case, implant spreader assembly 624 may be used to expand the sheet-like implant so that the sheet-like implant covers a treatment site within the body. First arm 620 and second arm 622 may move from the closed position shown in FIG. 16A to the open position shown in FIG. 16B to facilitate expansion of the sheet-like implant. First arm 620 and second arm 622 are also capable of moving from the open position shown in FIG. 16B to the closed position shown in FIG. 16A. In some applications, implant spreader assembly 624 may assume a lower profile configuration while implant delivery system 660 is withdrawn from the body.

With reference to FIG. 16A, it will be appreciated that first arm 620 and second arm 622 extend in a longitudinal direction that is generally parallel to a longitudinal axis 632 of delivery shaft 630 when the arms are in the closed position. By comparing FIG. 16B and FIG. 16A, it will be appreciated that the first arm 620 and second arm 622 move away from each other when moving from the closed position to the open position. In the embodiment of FIG. 16, first arm 620 and second arm 622 extend in a longitudinal direction that is generally parallel to longitudinal axis 632 when the arms are in the open position shown in the FIG. 16B.

An exemplary method in accordance with the present detailed description may include the step of affixing a sheet-like implant to first arm 620 and second arm 622 of implant spreader assembly 624. The sheet-like implant may be coupled to implant spreader assembly 624 in such a way that the implant is folded when the arms of implant spreader assembly 624 are in the closed position and unfolded when the arms of implant spreader assembly 624 are in the open position. The sheet-like implant may be delivered to a location proximate a treatment site within the body and implant spreader assembly 624 may also be used to unfold the sheet-like implant so that the sheet-like implant covers the treatment site.

Figure 17:
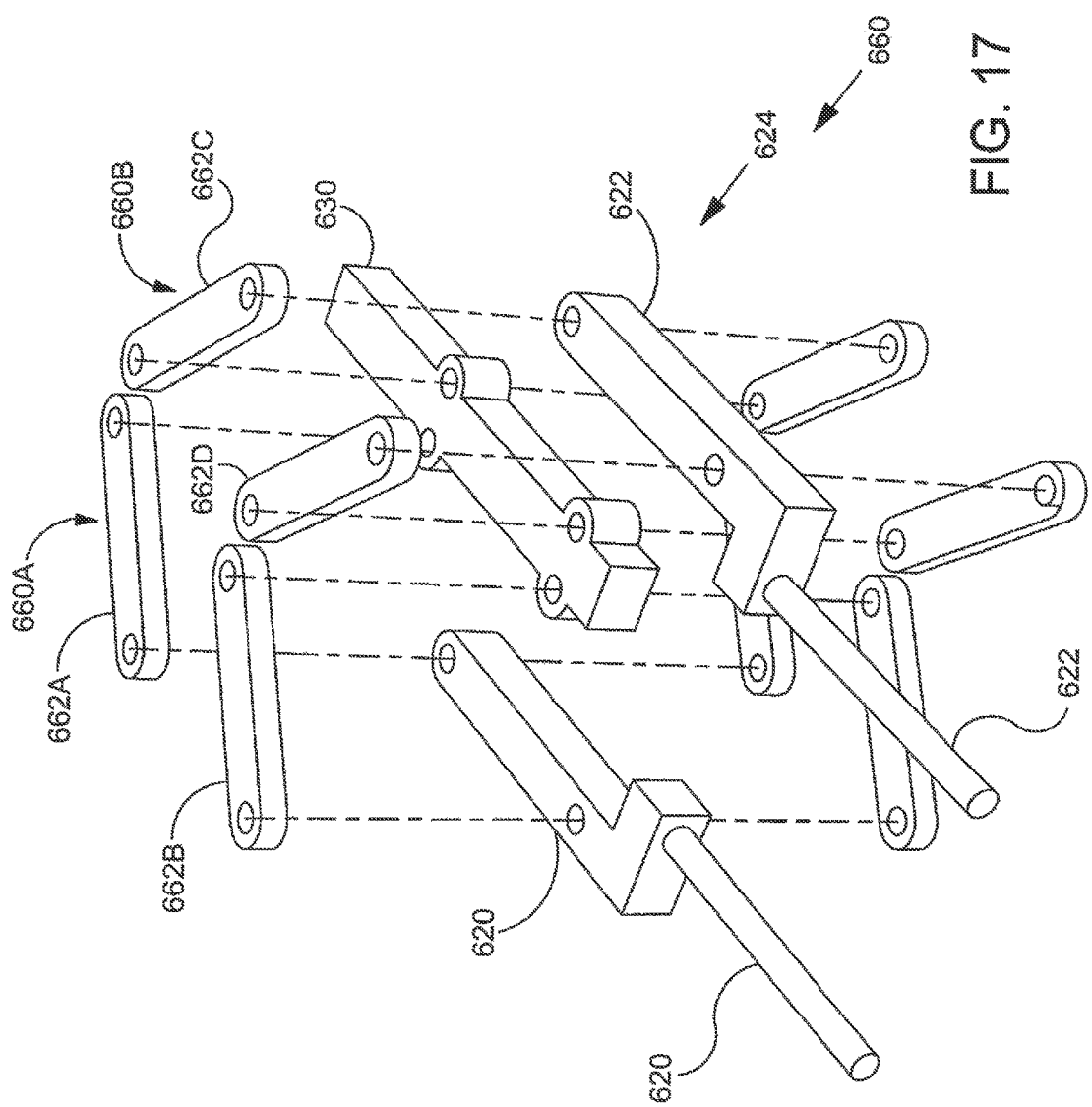
FIG. 17 is an exploded view further illustrating implant delivery system shown in the previous figure.

FIG. 17 is an exploded view further illustrating implant delivery system 660 shown in the previous figure. Implant delivery system 660 of FIG. 17 comprises an implant spreader assembly 624. In the embodiment of FIG. 17, implant spreader assembly 624 includes a first four bar linkage 660A and a second four bar linkage 660B. First four bar linkage 660A of implant spreader assembly 624 comprises first arm 620, a delivery shaft 630, a first link 662A and a second link 662B. Second four bar linkage 660A of implant spreader assembly 624 comprises second arm 622, a delivery shaft 630, a third link 662C and a fourth link 662D.

Figure 18:
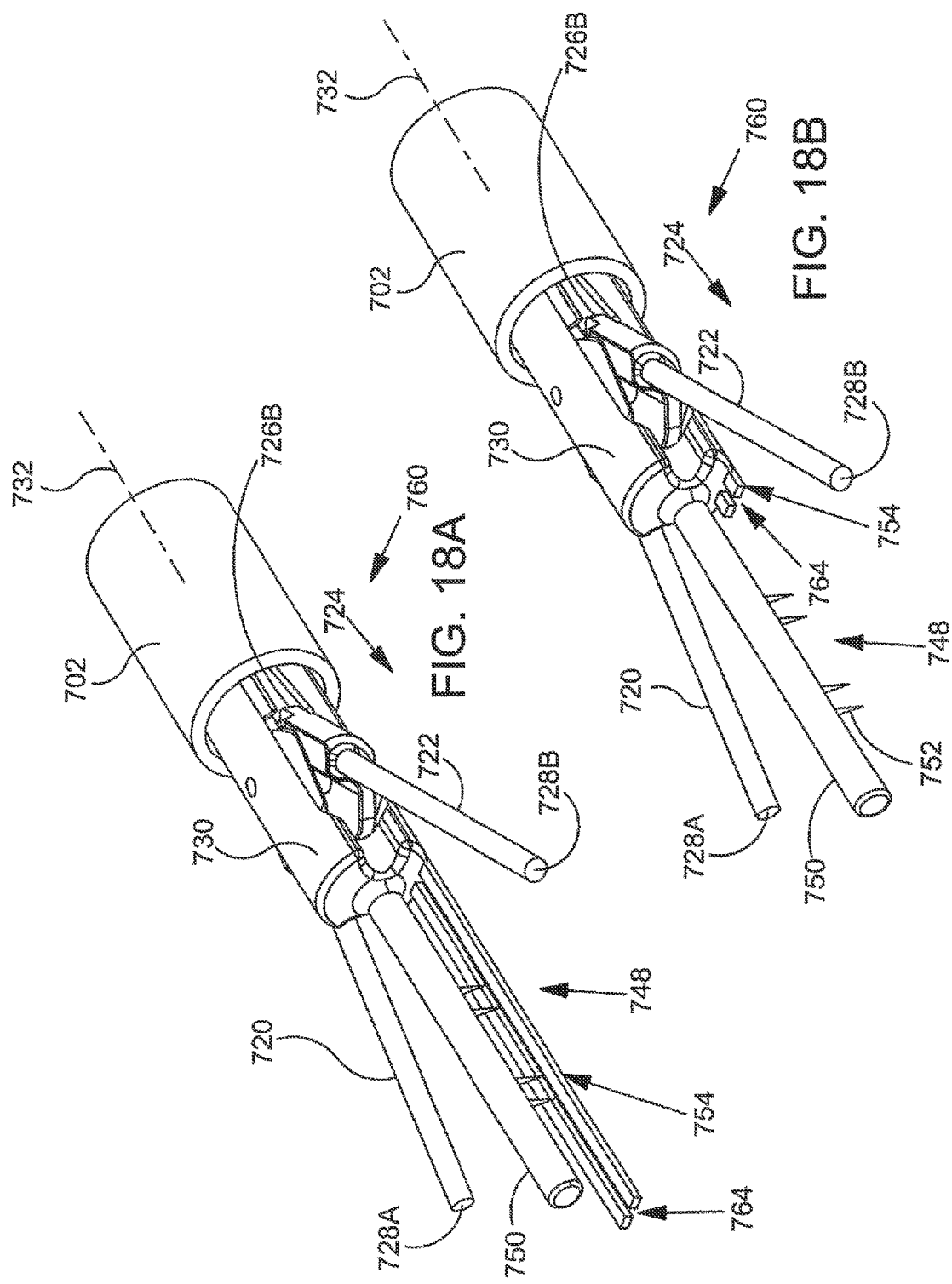
FIG. 18A and FIG. 18B are a pair of stylized perspective views illustrating another exemplary implant delivery system in accordance with the detailed description.

FIG. 18A and FIG. 18B are a pair of stylized perspective views illustrating another exemplary implant delivery system 760 in accordance with this detailed description. FIG. 18A and FIG. 18B will be collectively referred to as FIG. 18. Implant delivery system 760 comprises a delivery shaft 730 extending along a longitudinal axis 732. Implant delivery system 760 also includes an implant retainer assembly 748 and an implant spreader assembly 724 that are both located near a distal end of delivery shaft 730.

In the exemplary embodiment of FIG. 18, implant retainer assembly 748 comprises a center post 750 and a finger 754. A sheet-like implant may be positioned between center post 750 and finger 754 so that the implant is releasably coupled to implant retainer assembly 748 for positioning the sheet-like implant at a treatment site. In the exemplary embodiment of FIG. 18, center post 750 of implant retainer assembly 748 carries plurality of spikes 752. Finger 754 defines a channel 764 that is dimension to receive a distal portion of the spikes 752. In FIG. 18A, spikes 752 can be seen extending into channel 764 defined by finger 754.

In the embodiment of FIG. 18, finger 754 is capable of moving between an extended position (illustrated in FIG. 18A) and a retracted position (illustrated in FIG. 18B). Implant retainer assembly 748 is configured to releasably hold a sheet-like implant. Implant delivery system 760 may be used to deliver the sheet-like implant to a treatment site within a human body. Once the sheet-like implant is delivered to a location proximate the treatment site implant spreader assembly 724 may be used to unfold the sheet-like implant so that the sheet-like implant covers the treatment site.

Implant spreader assembly 724 of implant delivery system 760 comprises a first arm 720 and a second arm 722. First arm 720 has a proximal end and a distal end 728A. Second arm 722 has a distal end 728B and a proximal end 726B. The proximal end of each arm is pivotably connected to delivery shaft 730. First arm 720 and second arm 722 are moveable between a closed position and an open position. In FIG. 18, first arm 720 and second arm 722 are shown in the open position. When the arms are disposed in the closed position, the arms extend in a longitudinal direction that is generally parallel to longitudinal axis 732 of delivery shaft 730. When the arms pivot to the open position the distal end of each arm moves in a generally transverse direction. First arm 720 and second arm 722 may be used to spread an implant positioned on implant retainer assembly 748 as the arms pivot to the open position.

In the exemplary embodiment of FIG. 18A, implant delivery system 760 includes a sheath 702 disposed about delivery shaft 730. Sheath 702 is slidable in a direction generally parallel to longitudinal axis 732 of delivery shaft 730 such that sheath 702 can selectively cover and uncover implant spreader assembly 724, implant retainer assembly 748 and an implant held by implant retainer assembly 748. The implant may be rolled into a relatively compact shape so that the implant fits within the volume defined by sheath 702. Sheath 702 can be moved distally so that sheath 702 covers the implant when the implant is rolled into a relatively compact shape. Methods in accordance with this detailed description may include uncovering the implant (by withdrawing the sheath) and unrolling the implant using implant spreader assembly 724.

Figure 19:
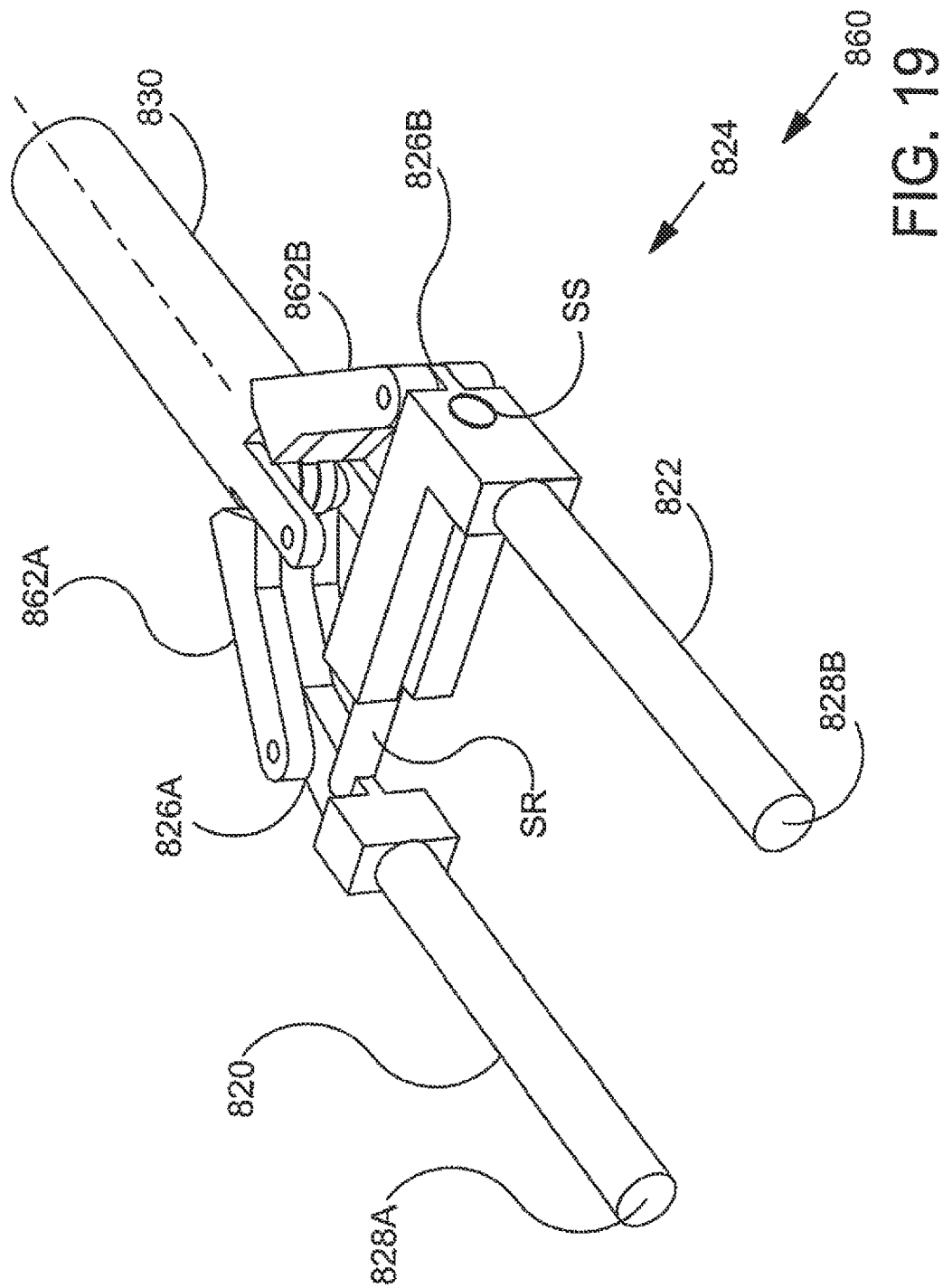
FIG. 19 is a stylized perspective view illustrating another exemplary implant delivery system in accordance with the detailed description.

FIG. 19 is a stylized perspective view illustrating another exemplary implant delivery system 860 in accordance with this detailed description. Implant delivery system 860 of FIG. 19 comprises a first arm 820 and second arm 822. First arm 820 and second arm 822 are both part of an implant spreader assembly 824. First arm 820 includes a proximal end 826A and a distal end 828A. In FIG. 19, a first link 862A can be seen extending between proximal end 826A of first arm 820 and a delivery shaft 830. Proximal end 826A of first arm 820 is pivotably coupled to a first end of first link 862A. A second end of first link 862A is pivotably coupled to delivery shaft 830. Second arm 822 of implant spreader assembly 824 has a proximal end 826B and a distal end 828B. Proximal end 826B of second arm 822 is pivotably coupled to a first end of a second link 862B. A second end of second link 862B is pivotably coupled to delivery shaft 830. In the embodiment of FIG. 19, first arm 820 comprises a slider rod SR that is slidingly received in a slider socket SS defined by second arm 822.

Figure 20:
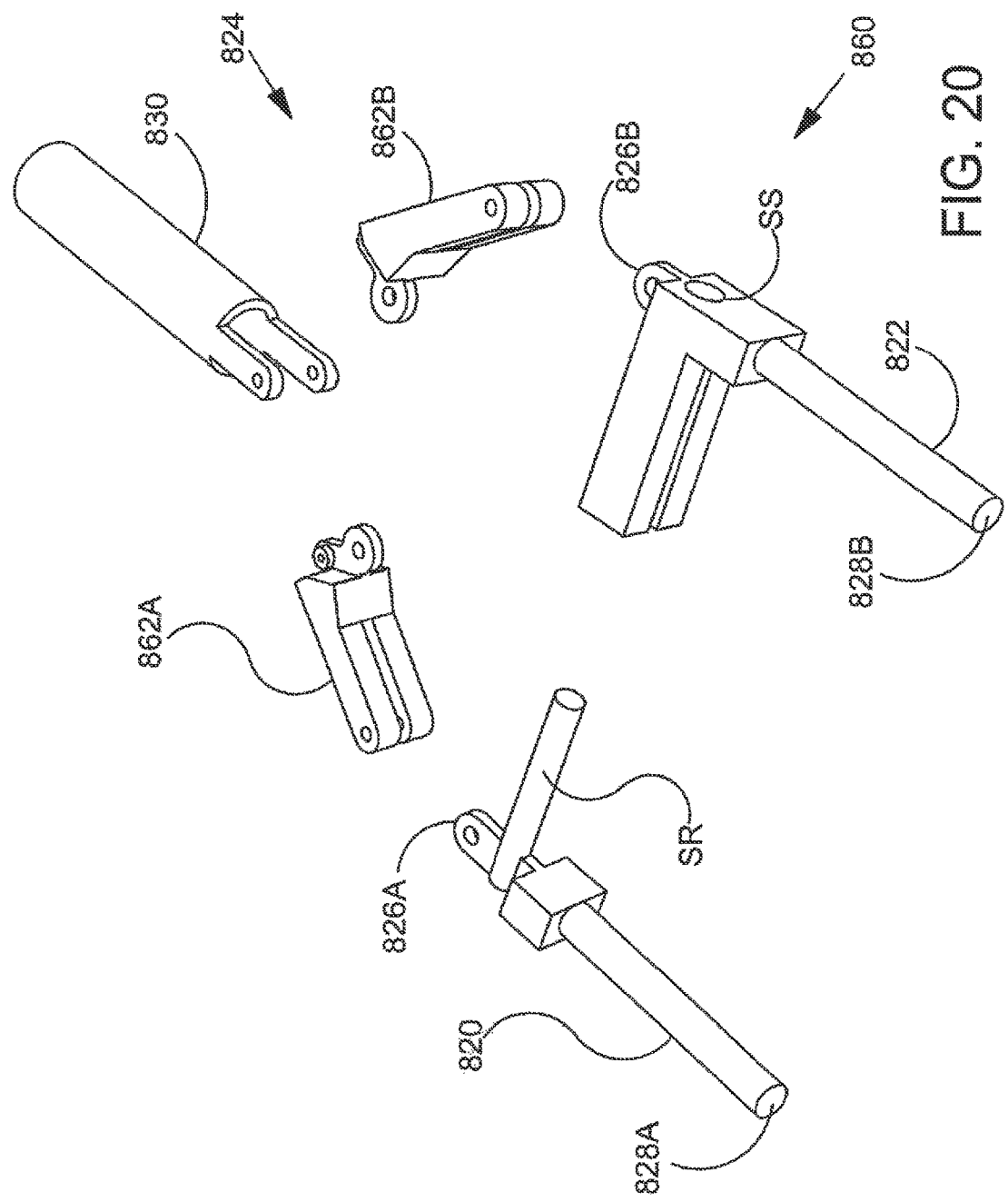
FIG. 20 is an exploded view further illustrating the implant delivery system shown in the previous figure.

FIG. 20 is an exploded view further illustrating implant delivery system 860 shown in the previous figure. Implant delivery system 860 of FIG. 20 comprises an implant spreader assembly 824. In the embodiment of FIG. 20, implant spreader assembly 824 includes a first arm 820, a second arm 822, a first link 862A and a second link 862B. First arm 820 includes a proximal end 826A and a distal end 828A. Proximal end 826A of first arm 820 is pivotably coupled to a first end of first link 862A when implant delivery system 860 is in an assembled state. A second end of first link 862A is pivotably coupled to delivery shaft 830 when implant delivery system 860 is in an assembled state. Second arm 822 of implant spreader assembly 824 has a proximal end 826B and a distal end 828B. Proximal end 826B of second arm 822 is pivotably coupled to a first end of a second link 862B when implant delivery system 860 is in an assembled state. A second end of second link 862B is pivotably coupled to delivery shaft 830 when implant delivery system 860 is in an assembled state. In the embodiment of FIG. 20, first arm 820 comprises a slider rod SR and second arm 822 comprises a slider socket SS. Slider rod SR is slidingly received in a slider socket SS when implant delivery system 860 is in an assembled state. With the embodiments of spreader assembly disclosed herein, a linkage assembly can be included that operably connects the spreader assembly to an actuation button or slide on the handle. The user can manipulate the spreader assembly between an open and a closed position via the linkage to the handle.

Figure 21:
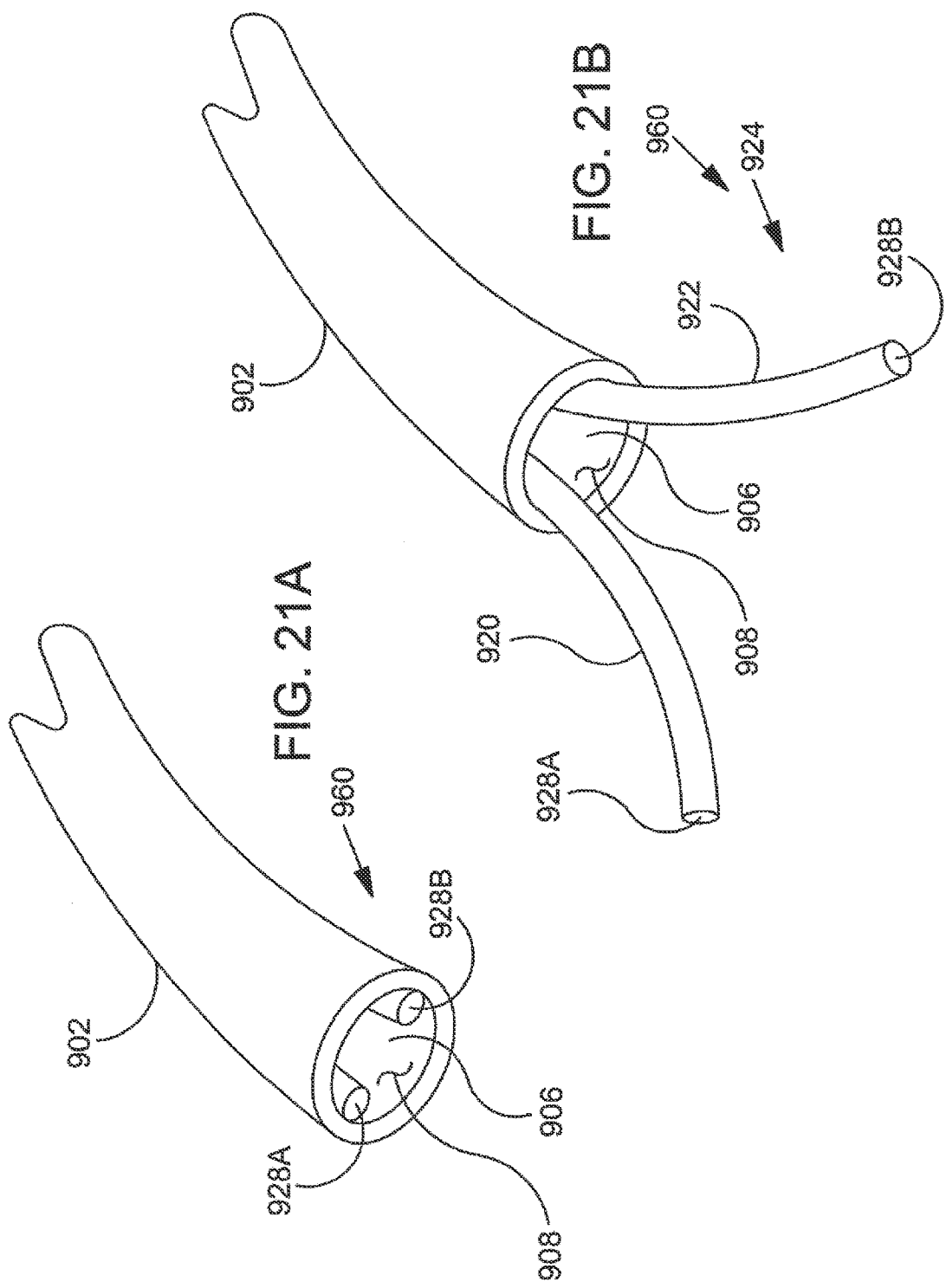
FIG. 21A and FIG. 21B are a pair of stylized perspective views illustrating another exemplary implant delivery system in accordance with the detailed description; and, FIG. 22 is a stylized perspective view of a shoulder including a supraspinatus muscle having a distal tendon.

FIG. 21A and FIG. 21B are a pair of stylized perspective views illustrating another exemplary implant delivery system 960 in accordance with this detailed description. FIG. 21A and FIG. 21B will be collectively referred to as FIG. 21. Implant delivery system 960 includes a sheath 902 defining a lumen 906 and a distal opening 908 fluidly communicating with lumen 906. In the embodiment of FIG. 21A, a first arm 920 and a second arm 922 are disposed in lumen 906. A distal end 928A of a first arm 920 and a distal end 928B of a second arm 922 can be seen residing in lumen 906 in FIG. 6A. In the embodiment of FIG. 21B, sheath 902 has been retracted proximally from around first arm 920 and second arm 922. By comparing FIG. 21B and FIG. 21A, it will be appreciated that distal end 928A of a first arm 920 and a distal end 928B of a second arm 922 have moved away from each other in generally transverse directions.

In the embodiment of FIG. 21, first arm 920 and second arm 922 are biased to assume the open position shown in FIG. 21B. In the embodiment of FIG. 21A, first arm 920 and second arm 922 are prevented from assuming the open position due to the restraining action of sheath 902. In the embodiment of FIG. 21B, first arm 920 and second arm 922 are unrestrained by sheath 902 so that first arm 920 and second arm 922 are free to assume the open position. In FIG. 21B, first arm 920 and second arm 922 are shown in an unstressed state in which no external forces are acting on first arm 920 and second arm 922.

First arm 920 and second arm 922 are both part of an implant spreader assembly 924. In some useful embodiments, a sheet-like implant is coupled to first arm 920 and second arm 922 of implant spreader assembly 924. When this is the case, implant spreader assembly 924 may be used to expand the sheet-like implant so that the sheet-like implant covers a treatment site within the body. First arm 920 and second arm 922 may move from the closed position shown in FIG. 21A to the open position shown in FIG. 21B to facilitate expansion of the sheet-like implant. First arm 920 and second arm 922 are also capable of moving from the open position shown in FIG. 21B to the closed position shown in FIG. 21A. In some applications, implant spreader assembly 924 may assume a lower profile configuration while implant delivery system 960 is withdrawn from the body.

An exemplary method in accordance with the present detailed description may include the step of affixing a sheet-like implant to first arm 920 and second arm 922 of implant spreader assembly 924. The sheet-like implant may be coupled to implant spreader assembly 924 in such a way that the implant is folded when the arms of implant spreader assembly 924 are in the closed position and unfolded when the arms of implant spreader assembly 924 are in the open position. The sheet-like implant may be delivered to a location proximate a treatment site within the body and implant spreader assembly 924 may be used to unfold the sheet-like implant so that the sheet-like implant covers the treatment site.

Figure 22:
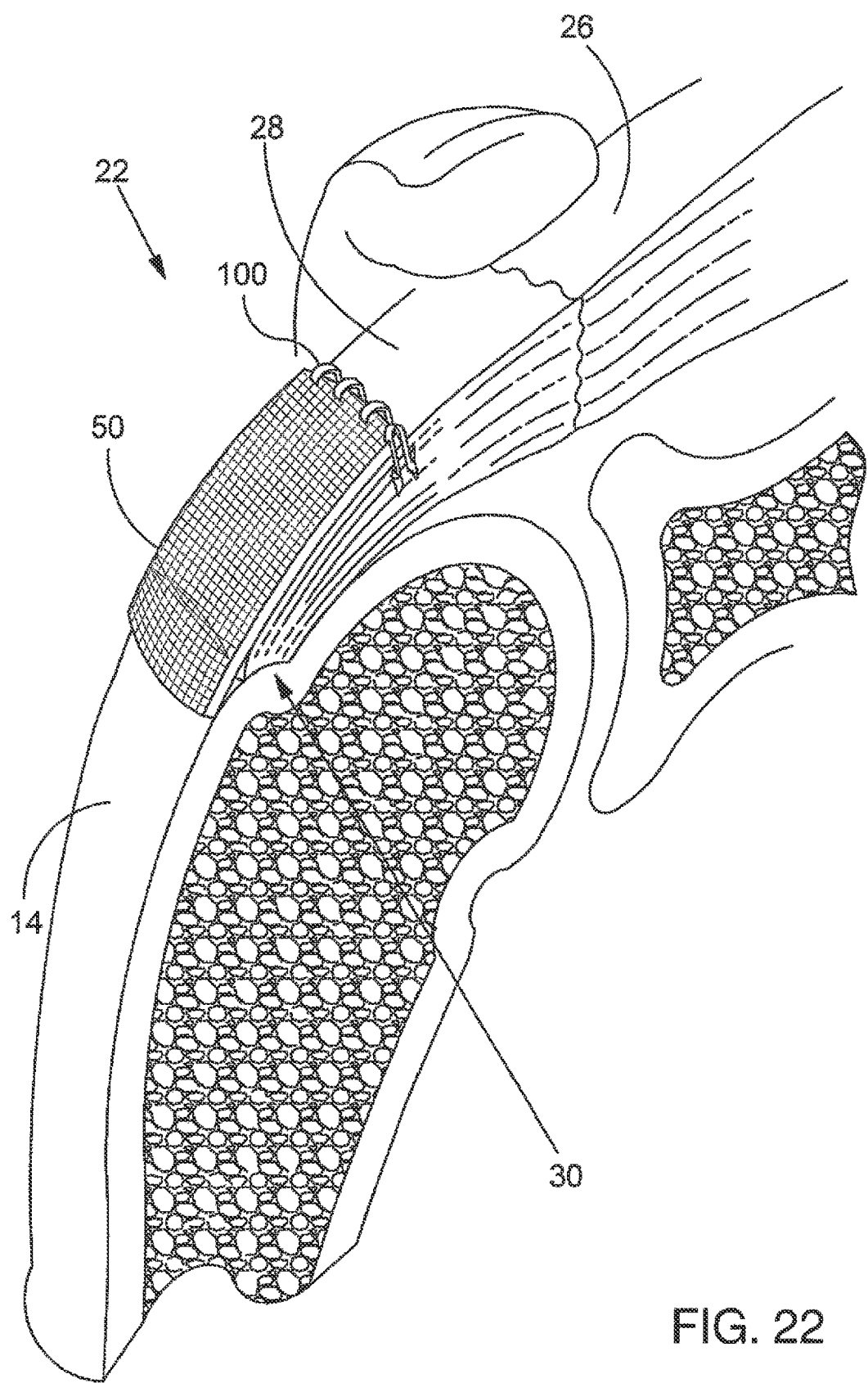

FIG. 22 is a stylized perspective view of a shoulder 22 including a supraspinatus 26 having a distal tendon 28. With reference to FIG. 22, it will be appreciated that a tendon repair implant 50 has been fixed to a surface of distal tendon 28. Tendon repair implant 50 may comprise, for example, various sheet-like structures without deviating from the spirit and scope of the present detailed description. In some useful embodiments, the sheet-like structure may comprise a plurality of fibers. The fibers may be interlinked with one another. When this is the case, the sheet-like structure may comprise a plurality of apertures comprising the interstitial spaces between fibers. Various processes may be used to interlink the fibers with one another. Examples of processes that may be suitable in some applications including weaving, knitting, and braiding. In some embodiment, the sheet-like structure may comprise a laminate including multiple layers of film with each layer of film defining a plurality of micro-machined or formed holes. The sheet-like structure of the tendon repair implant may also comprise a reconstituted collagen material having a porous structure. Additionally, the sheet-like structure of the tendon repair implant may also comprise a plurality of electro-spun nanofiber filaments forming a composite sheet. Additionally, the sheet-like structure may comprise a synthetic sponge material that defines a plurality of pores. The sheet-like structure may also comprise a reticulated foam material. Reticulated foam materials that may be suitable in some applications are available from Biomerix Corporation of Fremont, Calif. which identifies these materials using the trademark BIO-MATERIAL™. The sheet-like structure may be circular, oval, oblong, square, rectangular, or other shape configured to suit the target anatomy.

Various attachment elements may be used to fix tendon repair implant 50 to distal tendon 28 without deviating from the spirit and scope of this detailed description. Examples of attachment elements that may be suitable in some applications include sutures, tissue anchors, bone anchors, and staples. In the exemplary embodiment of FIG. 22, a plurality of staples are fixing tendon repair implant 50 to distal tendon 28. In some exemplary methods, a plurality of staples may be applied using a fixation tool. The fixation tool may then be withdrawn from the body of the patient. Distal tendon 28 meets humerus 14 at an insertion point 30. With reference to FIG. 22, it will be appreciated that sheet-like implant 50 extends over insertion point 30. Tendon repair implant may be applied to distal tendon 28, for example, using the procedure illustrated in the previous figures. In various embodiments, staples may straddle the perimeter edge of the sheet-like implant (as shown in FIG. 22), may be applied adjacent to the perimeter, and/or be applied to a central region of the implant. In some embodiments, the staples may be used to attach the implant to soft tissue and/or to bone.

While exemplary embodiments of the present invention have been shown and described, modifications may be made, and it is therefore intended in the appended claims and subsequently filed claims to cover all such changes and modifications which fall within the true spirit and scope of the invention.

What is claimed is:

1. An implant delivery system for delivering a sheet-like implant, the implant delivery system comprising:
   a sheet-like implant having a proximal edge and a distal edge;
   a delivery shaft having a proximal end and a distal end, the delivery shaft having a longitudinal axis;
   an implant spreader assembly proximate the distal end of the delivery shaft, the implant spreader assembly including a first arm and a second arm, the first arm and the second arm moveable between a closed position and an open position,
   wherein the first arm and the second arm are coupled to the sheet-like implant;
   wherein, in the closed position, proximal ends of the first arm and the second arm are secured to the distal end of the delivery shaft and distal ends of the first arm and the second arm are positioned at a first distance from the longitudinal axis;
   wherein, in the open position, the proximal ends of the first arm and the second arm are secured to the distal end of the delivery shaft and the distal ends of the first and second arms are positioned at a second distance from the longitudinal axis greater than the first distance;
   wherein in both the closed position and the open position the proximal edge of the sheet-like implant is a proximalmost portion of the sheet-like implant and the distal edge of the sheet-like implant is a distalmost portion of the sheet-like implant;
   wherein in both the closed position and the open position the distal ends of the first and second arms are at a distalmost extent of the implant spreader; and
   wherein the distal ends of the first and second arms are configured to diverge away from one another as the first and second arms move from the closed position to the open position to spread the sheet-like implant coupled to the first and second arm into an unfolded configuration.

2. The implant delivery system for delivering a sheet-like implant of claim 1, further comprising a sheath which is disposable about the implant spreader assembly in a first position in which the first arm and the second arm are in the closed position.

3. The implant delivery system for delivering a sheet-like implant of claim 2, wherein the sheath is configured to contain the sheet-like implant in a rolled configuration within the sheath when the sheath is in the first position and the first and second arms are in the closed position.

4. The implant delivery system for delivering a sheet-like implant of claim 3, wherein the sheath is moveable relative to the implant spreader assembly along the longitudinal axis to a second position in which the sheath is positioned proximal of the implant spreader assembly.

5. The implant delivery system for delivering a sheet-like implant of claim 2, wherein the sheath is configured to contain the sheet-like implant in a folded configuration within the sheath when the sheath is in the first position and the first and second arms are in the closed position.

6. The implant delivery system for delivering a sheet-like implant of claim 5, wherein the sheath is slideable relative to the implant spreader assembly along the longitudinal axis to a second position in which the sheath is positioned proximal of the implant spreader assembly.

7. The implant delivery system for delivering a sheet-like implant of claim 1, wherein the sheet-like implant extends tautly between the first arm and the second arm of the implant spreader assembly when the first and second arms are in the open position.

8. The implant delivery system for delivering a sheet-like implant of claim 1, wherein the sheet-like implant is sutured to the first and second arms.

9. An implant delivery device for delivering a sheet-like implant, the implant delivery device comprising:
   a sheet-like implant having a proximal edge and a distal edge;
   a delivery shaft having a proximal end, a distal end, and a longitudinal axis;
   a first arm disposed at the distal end of the delivery shaft and a second arm disposed at the distal end of the delivery shaft, the sheet-like implant attached to the first arm and attached to the second arm, wherein the first arm and the second arm are moveable between a closed position and an open position to transition the sheet-like implant from a folded configuration to an un-folded configuration; and
   wherein, in the closed position, proximal ends of the first arm and the second arm are secured to the distal end of the delivery shaft and distal ends of the first arm and the second arm are positioned at a first distance from the longitudinal axis;
   wherein, in the open position, the proximal ends of the first arm and the second arm are secured to the distal end of the delivery shaft and the distal ends of the first and second arms are positioned at a second distance from the longitudinal axis greater than the first distance;
   wherein in both the closed position and the open position the proximal edge of the sheet-like implant is a proximalmost portion of the sheet-like implant and the distal edge of the sheet-like implant is a distalmost portion of the sheet-like implant;
   wherein in both the closed position and the open position the distal ends of the first and second arms are at a distalmost extent of the first and second arms; and
   wherein the distal ends of the first and second arms are configured to diverge away from one another as the first and second arms move from the closed position to the open position to spread the sheet-like implant from the folded configuration to the un-folded configuration.

10. The implant delivery device of claim 9, wherein the first arm and the second arm each define a slot to releasably hold the sheet-like implant.

11. The implant delivery device of claim 10, wherein each of the first arm and the second arms comprises an upper finger and a lower finger with the slot located therebetween.

12. The implant delivery device of claim 9, further comprising a post extending distal of the delivery shaft along the longitudinal axis configured to position the sheet-like implant substantially parallel to the longitudinal axis of the delivery shaft.

13. The implant delivery device of claim 9, further comprising a sheath slideably disposed about the delivery shaft, the sheath having a first position and a second position, wherein, in the first position, the sheath is disposed about the first arm and the second arm preventing the first arm and the second arm from moving to the open position, and in the second position the sheath is disposed proximal of the first arm and the second arm allowing the first arm and the second arm to move to the open position.

14. The implant delivery device of claim 13, wherein when the sheath is in the first position, the sheath is configured to contain the sheet-like implant in the folded configuration within the sheath.

15. The implant delivery device of claim 13, wherein the first arm and the second arm self-actuate to move from the closed position to the open position when the sheath slides from the first position to the second position.

* * * * *